(12) United States Patent
Schenone et al.

(10) Patent No.: US 8,466,164 B2
(45) Date of Patent: *Jun. 18, 2013

(54) 4-SUBSTITUTED DERIVATIVES OF PYRAZOLO[3,4-D]PYRIMIDINE AND PYRROLO[2,3-D]PYRIMIDINE AND USES THEREOF

(75) Inventors: Silvia Schenone, Siena (IT); Francesco Bondavalli, Siena (IT); Olga Bruno, Siena (IT); Maurizio Botta, Siena (IT); Fabrizio Manetti, Siena (IT); Marco Radi, Siena (IT); Alessandra Santucci, Siena (IT); Giovanni Maga, Pavia (IT); Mauro Bologna, Siena (IT); Adriano Angelucci, Siena (IT); Annalisa Santucci, Siena (IT); Adriano Spreafico, Siena (IT); Fabio Carraro, Siena (IT); Jurgen Borlak, Lehrte (DE)

(73) Assignee: Universita degli Studi di Siena, Siena (IT)

( * ) Notice: Subject to any disclaimer, the term of this patent is extended or adjusted under 35 U.S.C. 154(b) by 129 days.

This patent is subject to a terminal disclaimer.

(21) Appl. No.: 12/678,021

(22) PCT Filed: Sep. 12, 2008

(86) PCT No.: PCT/IB2008/053689
§ 371 (c)(1),
(2), (4) Date: Mar. 12, 2010

(87) PCT Pub. No.: WO2009/034547
PCT Pub. Date: Mar. 19, 2009

(65) Prior Publication Data
US 2010/0249152 A1    Sep. 30, 2010

Related U.S. Application Data

(60) Provisional application No. 60/972,314, filed on Sep. 14, 2007.

(51) Int. Cl.
*A01N 43/90* (2006.01)
*A61K 31/519* (2006.01)
*C07D 487/00* (2006.01)

(52) U.S. Cl.
USPC ..................... 514/262.1; 544/262

(58) Field of Classification Search
None
See application file for complete search history.

(56) References Cited

U.S. PATENT DOCUMENTS 7,589,086 B2 * 9/2009 Bondavalli et al. ...... 514/217.06

FOREIGN PATENT DOCUMENTS

WO    2004/106339 A    12/2004

OTHER PUBLICATIONS

Carraro, et. al., Journal of Medicinal Chemistry (2004), 47(7), 1595-1598.*
Schenone, et. al., European Journal of Medicinal Chemistry (2004), 39(2), 153-160.*
Schenone, et al., "Antiproliferative activity of new 1-aryl-4-amino-1H-pyrazolo[3,4-d]pyrimidine derivatives toward the human epidermoid carcinoma A431 cell line.", European Journal of Medicinal Chemistry, 39(11):939-946, 2004.
Schenone, et al., "New pyrazolo[3,4-d]pyrimidines endowed with A431 antiproliferative activity and inhibitory properties of Src phosphorylation.", Bioorganic & Medicinal Chemistry Letters, 14(10):2511-2517, 2004.
Tuccinardi, et al., "Construction and validation of a RET TK catalytic domain by homology modeling,", Journal of Chemical Information and Modeling, 47(2):644-655, 2007.

* cited by examiner

*Primary Examiner* — Jeffrey Murray
(74) *Attorney, Agent, or Firm* — Lucas & Mercanti, LLP

(57) ABSTRACT

The present invention relates to a compound 4-substituted derivative of pyrazolo[3,4-d]pyrimidine or of pyrrolo[2,3-d]pyrimidine having the formula (I) and uses thereof, in particular for the treatment of bone related diseases and tumors.

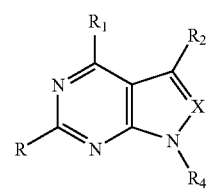

(I)

3 Claims, 26 Drawing Sheets

C

Figure 1:
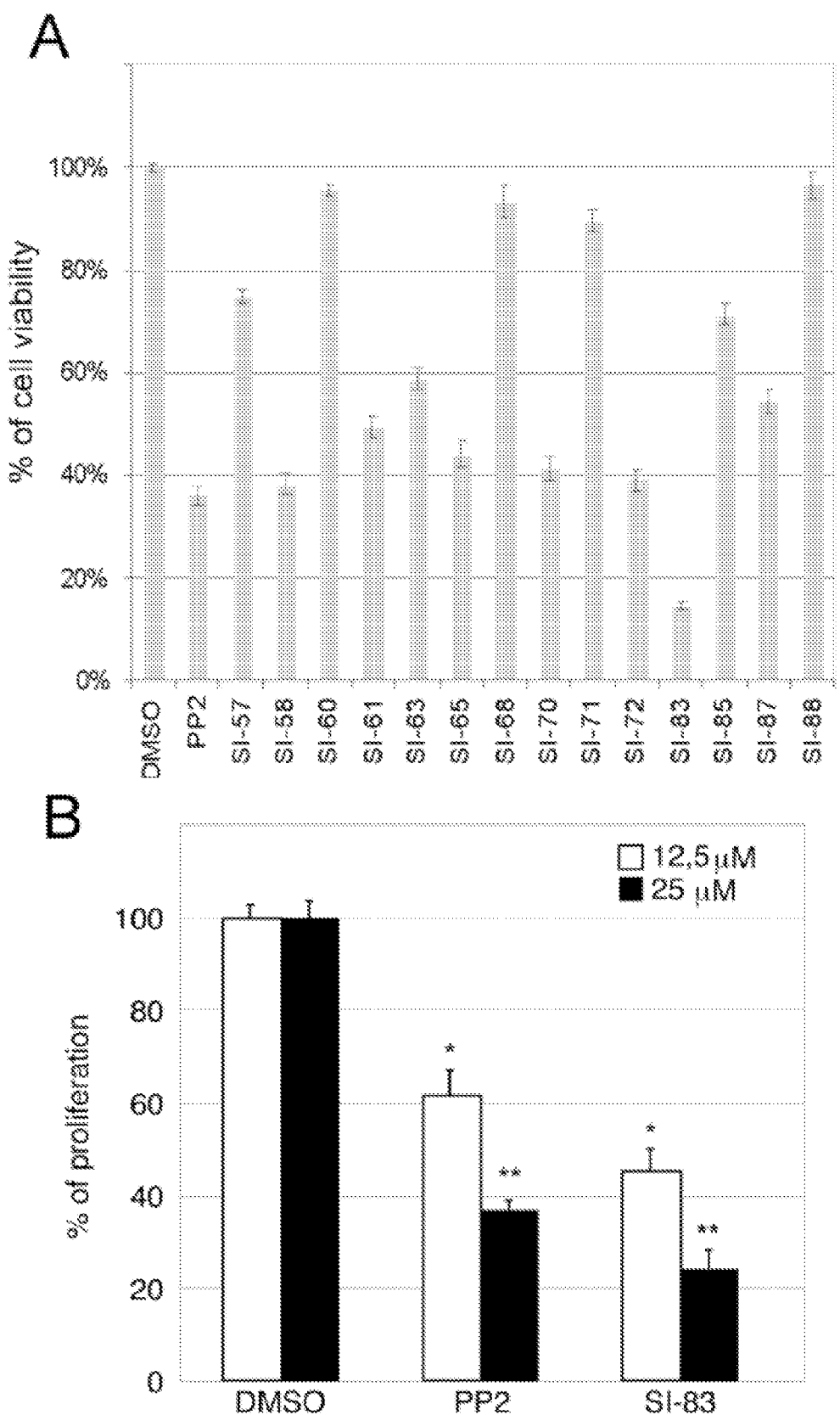

| Compound | Apoptosis | Phase G-2/M |
|---|---|---|
| DMSO | 2,58% | 5,01% |
| PP2 3 μM | 7,00% | 3,09% |
| PP2 IC$_{50}$ | 7,85% | 4,38% |
| PP2 25 μM | 8,85% | 3,57% |
| PP2 100 μM | 38,71% | 2,71% |
| SI-83 3 μM | 6,77% | 7,10% |
| SI-83 IC$_{50}$ | 17,21% | 2,03% |
| SI-83 25 μM | 43,20% | 3,05% |
| SI-83 100 μM | 45,11% | 1,01% |

Fig. 3 (cont)

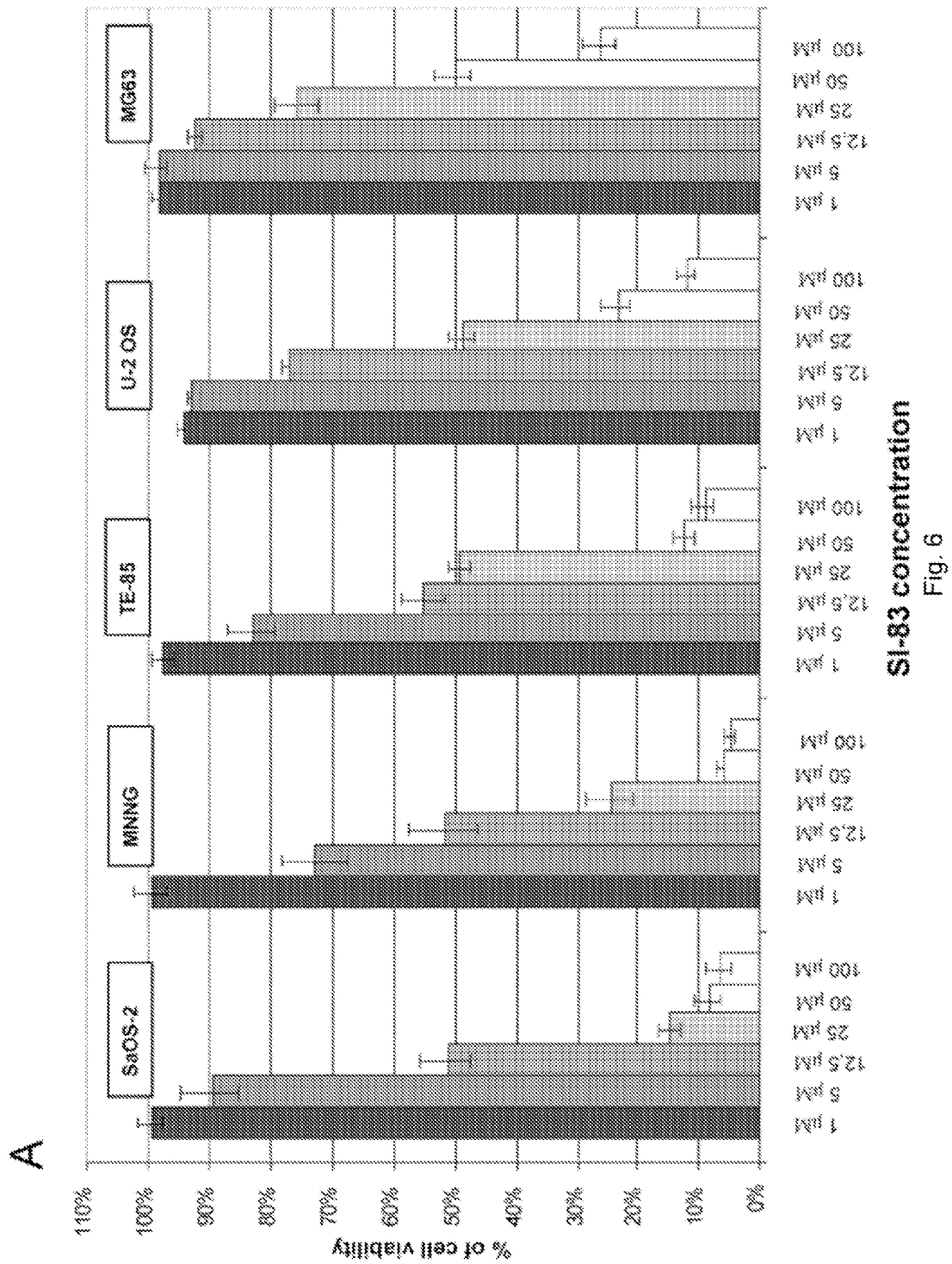

4-SUBSTITUTED DERIVATIVES OF PYRAZOLO[3,4-D]PYRIMIDINE AND PYRROLO[2,3-D]PYRIMIDINE AND USES THEREOF

CROSS-REFERENCE TO RELATED APPLICATIONS

This application is a 371 of PCT/IB2008/053689 filed Sep. 12, 2008, which claims the benefit of U.S. Provisional Application No. 60/972,314 filed Sep. 14, 2007, the contents of each of which are incorporated herein by reference.

FIELD OF THE INVENTION

The present invention refers to 4-amino-substituted pyrazolo[3,4-c/]pyrimidine derivatives, belonging to a new class of dual Src-Abl inhibitors, showing effects derived from targeting both Src (sarcoma) and Abl (Abelson) kinases. Such compounds proven to inhibit Src phosphorylation in a cell-free assay, thus significantly reducing the growth of human osteogenic sarcoma (SaOS-2) cells. They were also able to reduce bone resorption when used to treat mouse osteoclasts, without interfering with normal osteoblast growth. On the other hand by targeting Abl, they showed cytotoxic effects on Bcr (Breakpoint cluster region)-Abl-transduced cell lines (BaF3) resistant to Imatinib.

The compounds of the invention have therapeutic applications in particular for bone related diseases and or chronic myeloid leukemia (CML).

STATE OF THE ART

Over the past three decades, neoplastic diseases have been the second most common cause of death among western population, and the incidence rates have been increasing over time. Meanwhile, if the survival rates of cancer patients are increasing substantially, the incidence rates are still very high. The phenotype shift from standard to neoplastic is a substantially complex biological event, involving many alterations in cell physiology. Among them, transduction factor over expression has a critical role, and one of the most studied and interesting modifications are those involving over expression of Src tyrosine kinase (TK).

Targeted protein-tyrosine kinase inhibitors represent a major advance in cancer treatment. Although these drugs have been extremely effective in specific patient populations with tumors containing mutated, oncogenic forms of tyrosine kinases, the clinical experience suggests that most patients will develop resistance. Resistance can be caused by the amplification of the oncogenic protein kinase gene or other mechanisms and, in a significant fraction of cases, resistance can be traced to the selection of cancer cells with secondary mutations in the targeted kinase. The resistance mutations often appear in the kinase catalytic domain and directly prevent or weaken the interaction with the inhibitor drug. Consequently, it is important to develop efficient strategies to identify and rapidly develop alternative compounds that will be effective against mutated forms resistant to the first-line inhibitors.

Imatinib (4-[(4-methylpiperazin-1-yl)methyl]-N-[4-methyl-3-[(4-pyridin-3-ylpyrimidin-2-yl)amino]-phenyl]-benzamide represents the first choice drug for the treatment of Chronic Myeloid Leukemia (CML). Overcoming resistance to Imatinib remains a major challenge for successful treatment of CML, particularly in the advanced phases. Imatinib resistance in vivo and in vitro is mainly mediated by mutations within the Bcr-Abl kinase domain, by amplification of the Bcr-Abl signaling pathway or aberrant signals downstream of Bcr-Abl, such as those mediated by Src and Ras. Due to the high homology of Src and Abl kinases in their active conformation, Src inhibitors may be of additional therapeutic value for preventing or targeting drug resistance. Among them, Dasatinib was shown to be 325-fold more potent than Imatinib against wild-type Bcr-Abl and able to target most Imatinib-resistant Bcr-Abl mutations due to its conformation-tolerant binding to Abl kinase domain. Dasatinib is not effective against a mutant form of Bcr-Abl in which the threonine residue at position 315 is replaced by isoleucine (T315I). The T315 residue is referred to as the "gatekeeper" residue in protein kinases separating the ATP-binding site from an internal cavity. The T315I represents the primary resistant point mutation in Dasatinib-treated cases.

On the other hand, a variety of cellular signaling pathways involving protein kinases such as Src constitute the basis of the dynamic and highly regulated processes of bone remodeling which depend on osteoblasts and osteoclasts. The tyrosine kinase Src has been demonstrated to play a crucial regulatory role in both osteoblasts and osteoclasts. In particular, Src has been implicated as a negative regulator of osteoblast functional activity, based on the fact that reduction of Src expression stimulates osteoblast differentiation and bone formation.[1] Conversely, Src is also a mediator of anti-apoptotic signaling in osteoblasts, induced by various factors. As examples, Wnt proteins prevent apoptosis prolonging the survival of osteoblasts through the activation of the Src signaling cascade.[2] Moreover, anti-apoptotic effects of vitamin D3 analogues on the same cells are blocked by Src inhibitors such as the 4-amino-5-(4-methylphenyl)-7-(t-butyl)pyrazolo[3,4-d] pyrimidine (PP1).[3] Disruption of the src gene leads to osteopetrosis in mice,[4] due to the inability of osteoclasts to form ruffled borders and resorb bone during one of the final stages of their maturation (positive regulatory role of Src).[5] In addition, Src is also involved in signaling pathways leading to cell death of malignant osteoblasts (such as the osteosarcoma SaOS-2 cell line)[6] and contributes, in combination with paxillin, to the high metastatic potential of human osteosarcoma HuO9 cell line.[7] All these experimental evidences make Src as an attractive and promising therapeutic target for the treatment of bone related diseases such as osteoporosis,[8-10] osteosarcoma,[11] and cancer-induced bone metastasis.[7]

Literature of the last years reports a plethora of Src inhibitors originated from a variety of molecular scaffolds that have demonstrated potency up to the nanomolar range in enzymatic assays and high efficacy in animal models of bone disease. Such compounds are classified into SH2-SH3 domain inhibitors and kinase domain inhibitors. The first ones block protein-protein interactions between Src and other proteins involved in the signaling pathways. As an example, blocking the SH2 domain with high affinity might attenuate the excessive signal transduction in bone resorption diseases, such as osteoporosis and related bone diseases.[12] The second ones, inhibiting the kinase domain, mainly belong to 6-6 and 5-6 bicyclic cores, such as quinolines,[13] quinazolines,[14] pyrrolo[2,3-d]pyrimidine,[15] and pyrazolo[3,4-d]pyrimidine.[16]

The authors of the present invention have already designed and synthesized new class of pyrazolo[3,4-d]pyrimidine derivatives.[17] They have also found that some of such compounds were endowed with in vitro antiproliferative and pro-apoptotic activity toward epidermoid (A431) and breast cancer (8701-BC) cell lines, acting through the inhibition of c-Src (cellular Src) phosphorylation.[18]

Continuing their efforts in the design and synthesis of dual acting Src-Abl inhibitors, new pyrazolo[3,4-d]pyrimidines were obtained by the authors, that, on the basis of their previous findings, were expected to interfere with both Abl and Src activity. Accordingly, the compounds were evaluated in a cell-free Src assay. Moreover, considering the role of Src in osteoblast and osteoclast growth, compounds were also tested for their inhibitory properties toward human osteoblasts (both normal and osteosarcoma SaOS-2 cell lines) and osteoclasts. As a result, one compound (SI-83) emerged for its marked ability to reduce the viability of SaOS-2 cells in vitro, without affecting normal osteoblasts. It also showed metabolic stability in a Tier 1 metabolic stability screen. These experimental findings prompted us to test it on a human SaOS-2 xenograft tumor in nude mice, finding a significant reduction of both the volume and weight of tumor.

Moreover, compounds were also tested for their ability to inhibit mutant forms of Bcr-Abl and found to be active toward the T315I mutant, resistant to Imatinib and Desatinib.

Thus, the new compounds are considered as potential agents in the treatment of osteosarcoma and osteoclast-related bone diseases, as well as antileukemic agents, overcoming resistance to Imatinib in the treatment of CML.

Another aspect of the present invention relates to the specific targeting of cancer stem cells. Cancer cells heterogeneity has been demonstrated as one of the possible causes for tumor (re)growth or resistance to current pharmacological therapies.[19] Especially solid tumors has been shown to contain a distinct population of tumorigenic cells with the exclusive ability to form tumors in mice.[20] The ability to target separately tumorigenic and nontumorigenic populations of tumor cells may have prognostic significance for patients with cancer.

To test their molecules for targeting cancer partially differentiated cells, which could represent the population responsible for the growth and resistance of tumours, the authors isolated spontaneously-transformed tumor cells from mice double transgenic for c-Myc and c-Raf Cells were isolated from lung tumors of eight-month-old transgenic mice.[21]

Having these tumor-derived cell lines available, the cytotoxicity of 4-amino-substituted pyrazolo[3,4-d]pyrimidine derivatives was investigated. These compounds clearly showed the capacity to inhibit proliferation of undifferentiated tumor stem/progenitor cells (with different strength, depending on the different progenitor tumor/stem cells line considered). For these reasons, such molecules, used alone or in synergy (cocktail), are suitable for the treatment of cancers which do not respond to current therapies.

DETAILED DESCRIPTION OF THE INVENTION

The present invention refers to 4-amino-substituted pyrazolo[3,4-d]pyrimidine derivatives, belonging to a new class of dual Src-Abl inhibitors. Such compounds inhibit Src phosphorylation in a cell-free assay, thus significantly reducing the growth of human osteogenic sarcoma (SaOS-2) cells. They are also able to reduce bone resorption when used to treat mouse osteoclasts, without interfering with normal osteoblast growth. Moreover, their metabolic stability prompted us to study it on a human SaOS-2 xenograft tumor model in nude mice where the compound reduced significantly both volume and weight of the tumor. These experimental findings make the new compounds as an interesting hit in the field of bone related diseases.

The present invention also describes the pro-apoptotic activity of novel Src inhibitor compounds toward human osteosarcoma, a very aggressive malignant tumour for which an effective treatment has still to be found. In particular, one compound showed antiproliferative and pro-apoptotic activities better than the reference compound PP2, showing also selectivity towards cancer cells, being its action far lower on human primary osteoblasts, the normal cell counterpart of this tumour. This latter finding is of remarkable importance since anti-cancer drugs are not frequently tested on non-neoplastic cells where usually treatments have negative effects as well. The authors also suggest that this type of compounds could have an optimal application on osteoblastic cells where Src is normally downregulated, thus reducing undesirable side effects. This low toxicity was also confirmed by in vivo experiments proving a significant reduction of tumour mass of a human osteosarcoma xenograft in a murine model.

Therefore it is an object of the invention a compound 4-substituted derivative of pyrazolo[3,4-d]pyrimidine or of pyrrolo[2,3-d]pyrimidine having the formula:

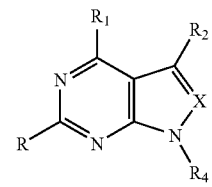

X represents CH or N;
R represents H, alkylthio, alkylamino, cycloalkyl, cycloalkylthio, cycloalkylamino, alkyl, $S(CH_2)_nOH$, $S(CH_2)_nNH_2$, $NH(CH_2)_nOH$, $NH(CH_2)_nNH_2$;
$R_1$ represents $NH-R_6$ or $N(R_6)_2$;
$R_6$ represents an alkyl, cycloalkyl, 1-pyrrolidinyl, 4-morpholinyl, 1-hexahydroazepinyl Or an aryl with the formula:

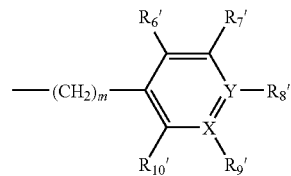

in which X and Y are independently H or N;
in which $R_6'$, $R_7'$, $R_8'$, $R_9'$, $R_{10}'$ are independently H, $C_{1-6}$ alkyl, $C_{2-6}$ alkenyl, $C_{2-6}$ alkynyl, aryl substituted groups, halo, haloalkyl, $OCH_3$, $NO_2$, $CN$, $CONH_2$, $CONH-C_{1-6}$ alkyl, $CON(C_{1-6}alkyl)_2$, $NH_2$, $NH-C_{1-6}$ alkyl, $N(C_{1-6}$ alkyl$)_2$, $NHC(O)alkyl$, $NHSO_2-C_{1-6}$ alkyl, $SO_2NH_2$, $SO_2NHC_{1-6}$ alkyl, $SO_2N(C_{1-6}$ alkyl$)_2$, $OZ'$ or $SZ'$ where $Z'$ is H, or alkyl, aryl o aralkyl substituted group,
m is comprised between 0 and 4;
$R_6$ represents also an aryl with the formula:

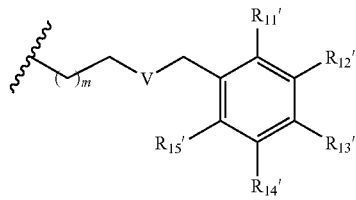

in which V is N, S, O;

$R_{11}'$, $R_{12}'$, $R_{13}'$, $R_{14}'$, $R_{15}'$ are independently H, $C_{1-6}$ alkyl, $C_{2-6}$ alkenyl, $C_{2-6}$ alkynyl, aryl substituted groups, halo, haloalkyl, $OCH_3$, $NO_2$, CN, $CONH_2$, $CONH$—$C_{1-6}$ alkyl, $CON(C_{1-6}$ alkyl$)_2$, $NH_2$, $NH$—$C_{1-6}$ alkyl, $N(C_{1-6}$ alkyl$)_2$, NHC(O)alkyl, $NHSO_2$—$C_{1-6}$ alkyl, $SO_2NH_2$, $SO_2NHC_{1-6}$ alkyl, $SO_2N(C_{1-6}$ alkyl$)_2$, OZ' or SZ' where Z' is H, or alkyl, aryl o aralkyl substituted groups;

m is comprised between 0 and 4;

$R_2$ represents H or an aryl with the formula:

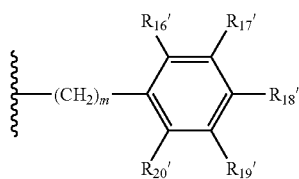

in which $R_{16}'$, $R_{17}'$, $R_{18}'$, $R_{19}'$, $R_{20}'$ are independently H, $C_{1-6}$ alkyl, $C_{2-6}$ alkenyl, $C_{2-6}$ alkynyl, aryl substituted groups, halo, haloalkyl, $OCH_3$, $NO_2$, CN, $CONH_2$, $CONH$—$C_{1-6}$ alkyl, $CON(C_{1-6}$ alkyl$)_2$, $NH_2$, $NH$—$C_{1-6}$ alkyl, $N(C_{1-6}$ alkyl$)_2$, NHC(O)alkyl, $NHSO_2$—$C_{1-6}$ alkyl, $SO_2NH_2$, $SO_2NHC_{1-6}$ alkyl, $SO_2N(C_{1-6}$ alkyl$)_2$, OZ' or SZ' where Z' is H, or alkyl, aryl o aralkyl substituted groups;

m is comprised between 0 and 4;

$R_4$ represents

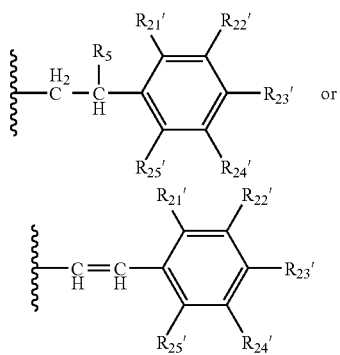

wherein $R_{21}'$, $R_{22}'$, $R_{23}'$, $R_{24}'$, $R_{25}'$ are independently H, $C_{1-6}$ alkyl, $C_{2-6}$ alkenyl, $C_{2-6}$ alkynyl, aryl substituted groups, halo, haloalkyl, $OCH_3$, $NO_2$, CN, $CONH_2$, $CONH$—$C_{1-6}$ alkyl, $CON(C_{1-6}$ alkyl$)_2$, $NH_2$, $NH$—$C_{1-6}$ alkyl, $N(C_{1-6}$ alkyl$)_2$, NHC(O)alkyl, $NHSO_2$—$C_{1-6}$ alkyl, $SO_2NH_2$, $SO_2NHC_{1-6}$ alkyl, $SO_2N(C_{1-6}$ alkyl$)_2$, OZ' or SZ' where Z' is H, or alkyl, aryl o aralkyl substituted groups;

$R_5$ represent Cl, Br, OH, H, $CH_3$.

In one embodiment of the invention, the compound of the invention is used as medicament, preferably as an anti-tumour and/or anti-leukaemia agent. More particularly, the compound is used for the treatment of CML resistant to Imatinib.

It is another object of the invention a pharmaceutical composition comprising at least one of the compounds of the invention or a pharmaceutically acceptable salt thereof, and suitable excipients and/or diluents.

It is also an object of the invention a method for the treatment of a tumour including the therapeutic administration of the compound of the invention.

Compounds of the invention or their salts may be administered as pure or as pharmaceutical formulations, i.e. suitable for parenteral, oral, or rectal administrations. Each of said formulations may contain excipients and/or fillers and/or additives and/or binders, coatings and/or suspending agents and/or emulsifying agents, preserving and/or control release agents, suitable for the selected pharmaceutical form.

The present invention reports the capacity of SI compounds to inhibit proliferation of undifferentiated tumor stem/progenitor cells (with different strength, depending on the different progenitor tumor/stem cells line considered). Therefore, such molecules used alone or in synergy (cocktail), are suitable for the treatment of cancers which do not respond to current therapies.[19]

The invention will be now illustrated by means of non limiting examples referring to the following figures:

FIG. 1—A) Effects of pyrazolo[3,4-d]pyrimidine derivatives on SaOS-2 cell viability measured by MTT assay. Data are expressed as percentage values respecting to DMSO, used as vehicle. PP2 was assayed as a reference compound at the same concentrations of pyrazolo[3,4-d]pyrimidine derivatives. Cells were treated with compounds (25 µM) for 48 h. Values are means±SEM of three independent experiments performed in triplicates. Error bars show the SDs from the mean values. B) Proliferation inhibitory effects of compounds PP2 and SI-83 measured by BrdU incorporation assay. Cells were treated with compounds at 25 µM and 12.5 µM for 24 h. Values are means±SEM of three independent experiments performed in triplicates. Error bars show the SDs from the mean values. *=P<0.05 versus DMSO-treated cells. **=P<0.05 versus DMSO-treated cells.

Figure 2:
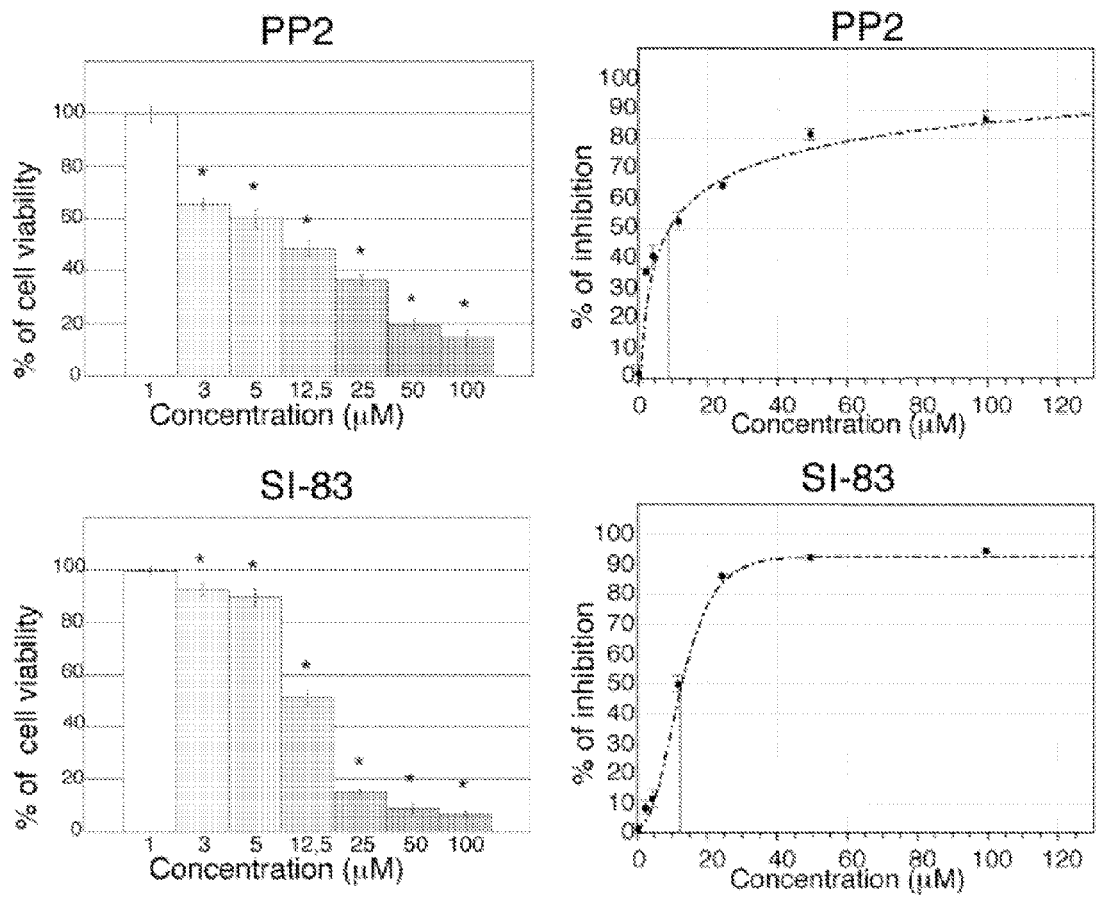

FIG. 2—Determination of $IC_{50}$ values for PP2 and SI-83 on SaOS-2 cells. Cell viability inhibitory effects of compounds were measured by the MTT assay, in a concentration range of 1-100 µM. Data are expressed as percentage values respecting to control, DMSO (left panels). In right panels the corresponding curves of inhibition are reported. Values are means±SEM of three independent experiments performed in triplicates. Error bars show the SDs from the mean values. *=P<0.05 versus DMSO-treated cells. $IC_{50}$ values are reported in the table. Graphical representation and $IC_{50}$ values were obtained by the software Curve Expert 1.3.

Figure 3:
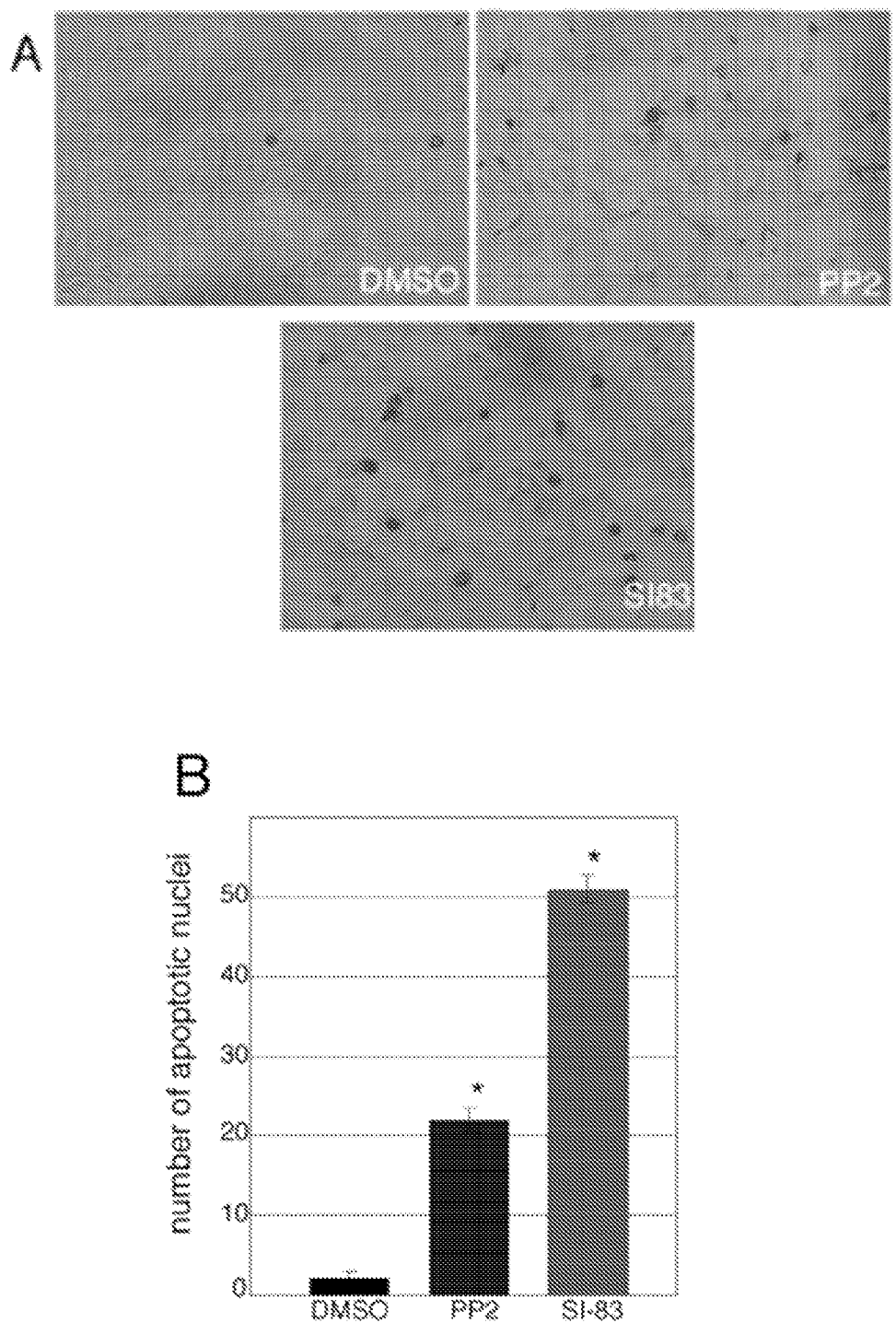
Figure 3:
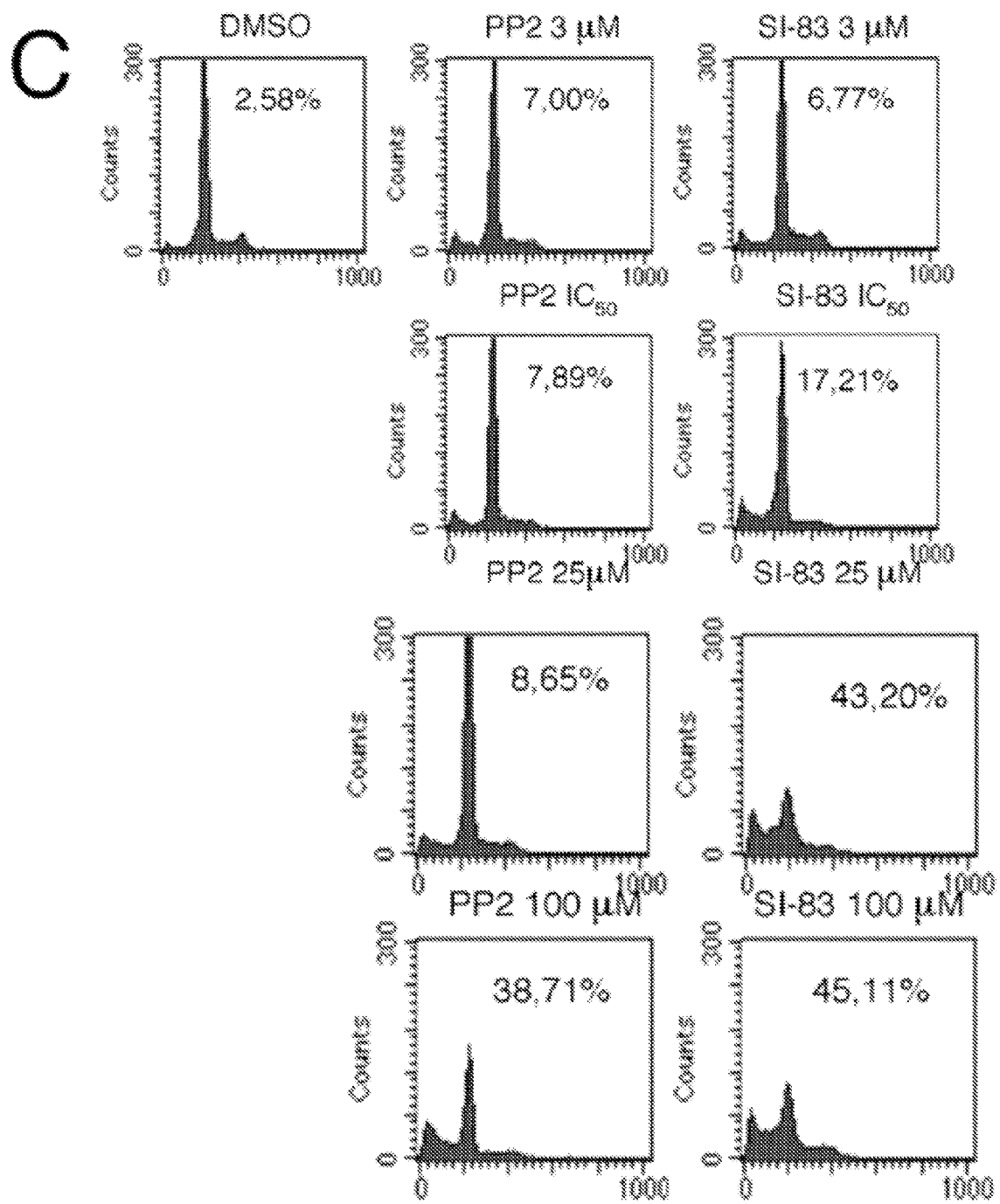
Figure 3:
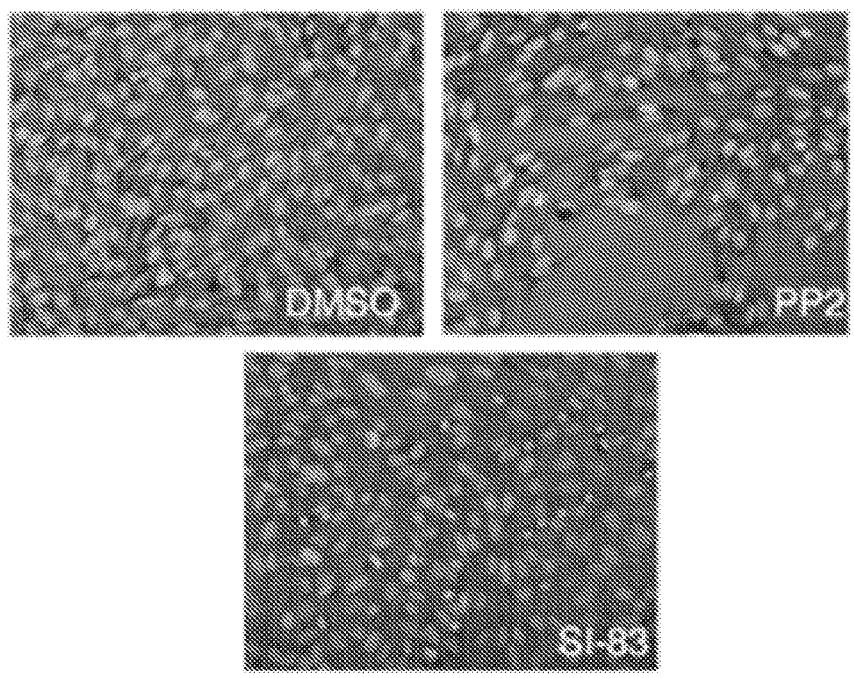

FIG. 3—Pro-apoptotic effects of Src inhibitors on SaOS-2 cells. A) TUNEL assay of SaOS-2 cells after treatment with PP2 and SI-83 at 12.5 µM for 48 h. Apoptotic nuclei are stained and appear dark. Original magnification of photograph is 40×. A representative experiment is reported. B) Number of apoptotic nuclei counted from five independent optical microscope fields of the experiment described in A. The results are representative of three independent experiments and for each one P is <0.05 versus DMSO-treated cells. C) Flow cytometric analysis of SaOS-2 cells treated with PP2 and SI-83 for 48 h. Compounds were used at 3 µM, 12.5 µM, $IC_{50}$, 25 µM, 100 µM. The vertical axis represents the relative number of events and the horizontal axis the fluorescence intensity. The percentages indicate the relative number of apoptotic cells. The results shown are representative of three independent experiments. Values of induced apoptosis and relative percentage for G2/M phase are reported in the Table. D) SaOS-2 cells were treated with PP2 and SI-83 for 48 h at 25 mM, stained with Hoechst and observed at a microscope. Scale bar 30 µm.

Figure 4:
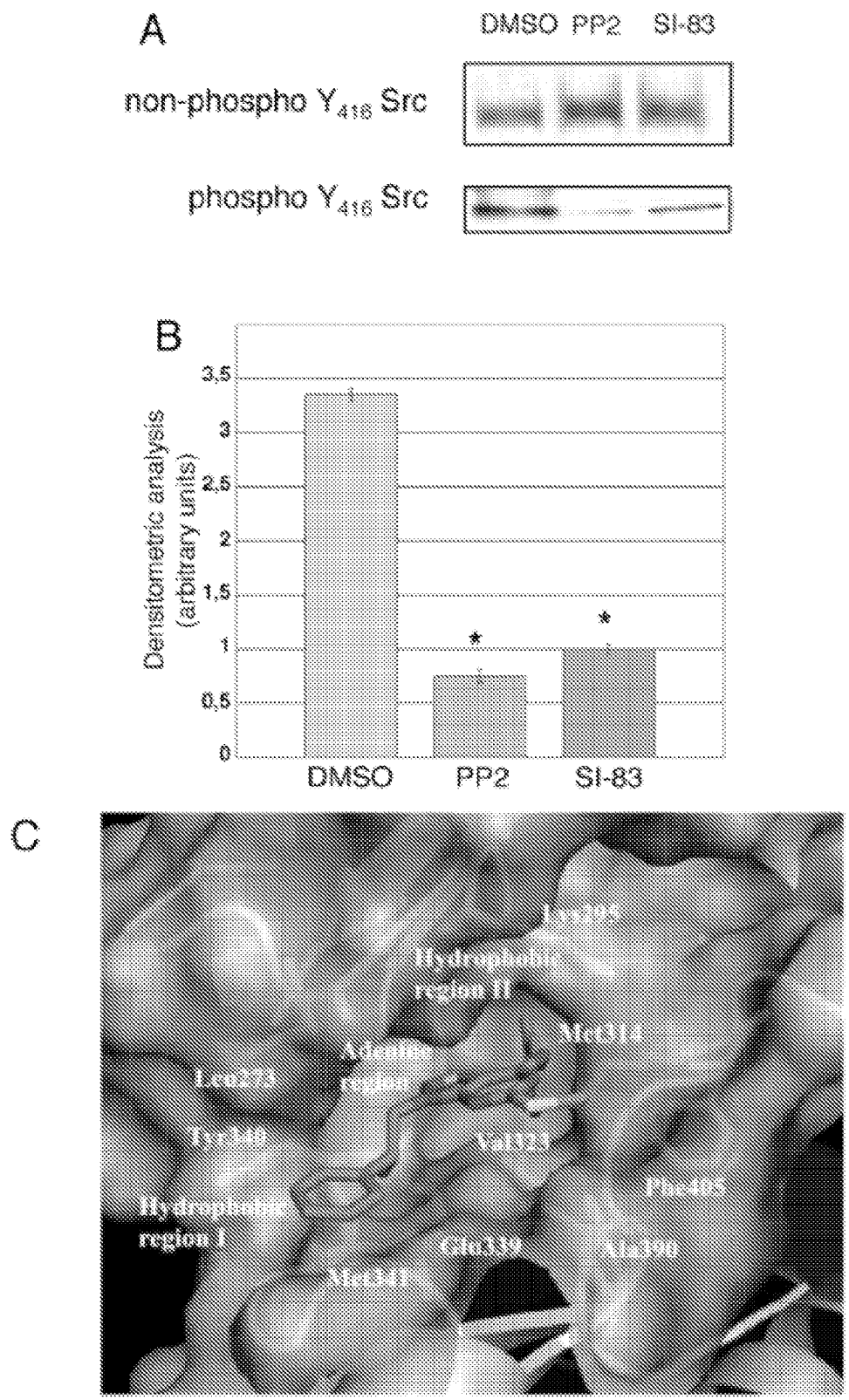

FIG. 4—Src-Tyr416 phosphorylation is decreased after PP2 and SI-83 treatment. Compounds were used at their corresponding $IC_{50}$. Cells were treated for 3 h prior to their lysis. A) Specific c-Src phosphorylation was evaluated when whole-cell lysates were immunoprobed with anti-nonphospho-Src-Y416 and anti-phospho-Src-Y416 antibodies. B) Graph reports the optical density values relative to immunoreactive bands of phospho-Src-Y416. Values are means±SEM of three independent experiments performed in triplicates. Error bars show the SDs from the mean values. *=P<0.05 versus DMSO-treated cells. C) Graphical representation of SI-83 (magenta) into the ATP binding pocket of Src. The solvent accessible surface of residues is depicted (blue), while several amino acids, responsible for the major hydrophobic contacts with the binding site, are also shown (cyan).

Figure 5:
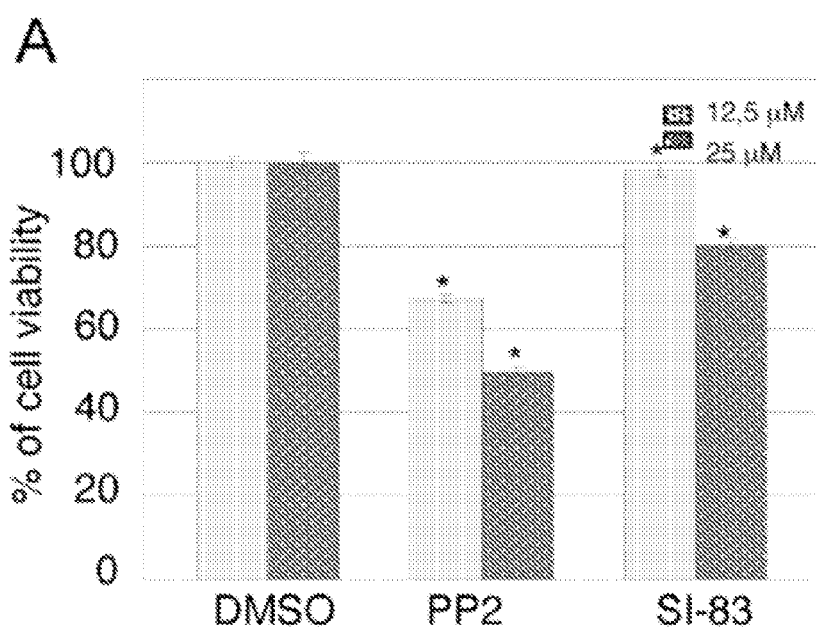
Figure 5:
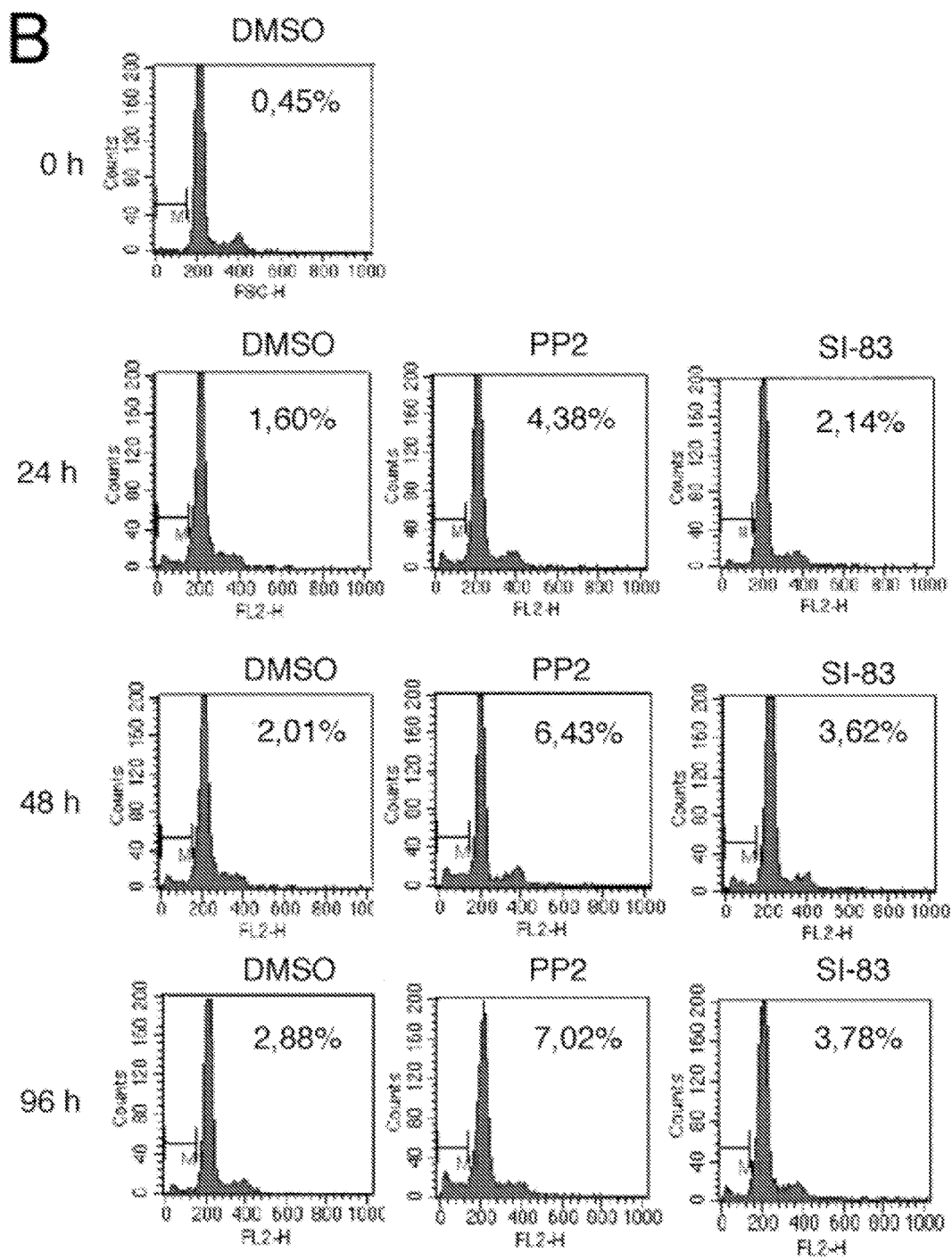
Figure 5:
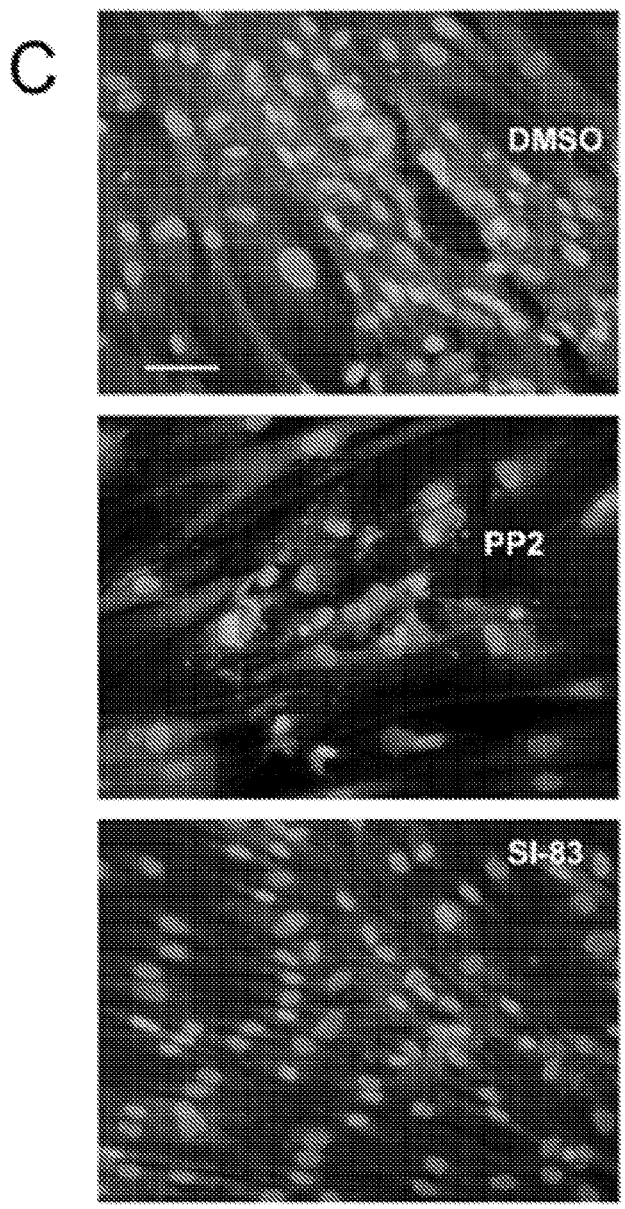
Figure 5:
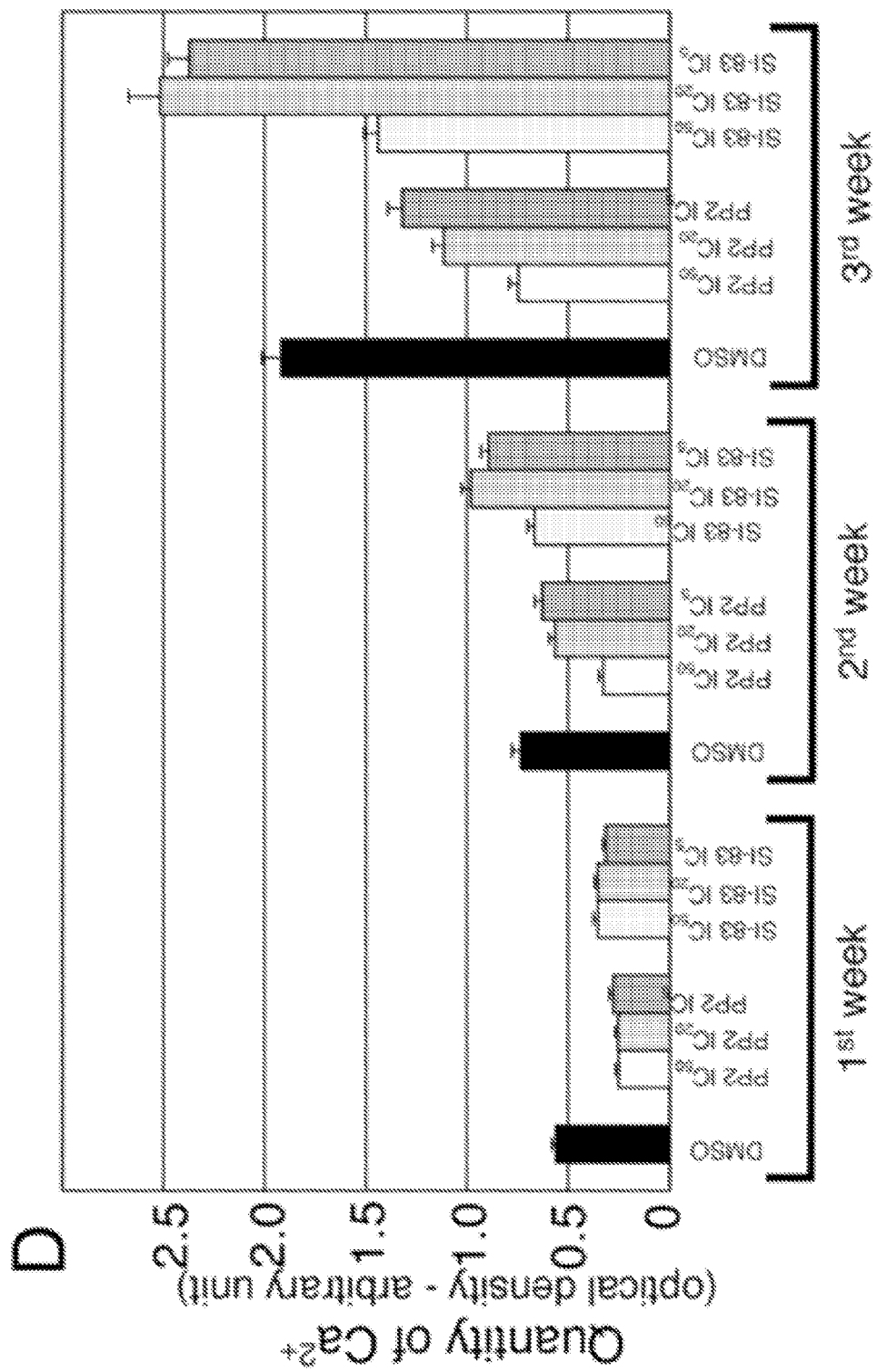

FIG. 5—Cell viability and pro-apoptotic effects of Src inhibitors on primary human osteoblasts A) Effects of pyrazolo[3,4-d]pyrimidine derivatives on cell viability of human primary osteoblasts, measured by MTT assay. Data are expressed as percentage of control (vehicle). Cells were treated with compounds for 48 h. Values are means±SEM of three independent experiments performed in duplicates. Error bars show the SDs from the mean values. *=P<0.05 versus DMSO-treated cells. B) Flow cytometric analysis of human osteoblasts treated for 24, 48 and 96 h with PP2 and SI-83, at their corresponding $IC_{50}$. Flow cytometric analysis was performed by DNA staining with propidium iodide. The vertical axis represents the relative number of events and the horizontal axis the fluorescence intensity. The percentages indicate the relative number of apoptotic cells. The results shown are representative of three independent experiments. C) Hoechst staining of human primary osteoblasts treated for 24 h with PP2 and SI-83, at a concentration of 25 µM. Scale bar 30 µm. D) Effects of different concentrations of PP2 and SI-83 on normal human osteoblast cell mineralization. The degree of mineralization was determined after 1, 2 and 3 weeks, using the alizarin red S method. The compounds were added at concentrations corresponding to $IC_5$, $IC_{20}$ and $IC_{50}$, previously calculated on SaOS-2 cells. Administration of compounds was twice a week. After each week, cells were stained for mineralization nodules with alizarin red S and $Ca^{2+}$ deposition was evaluated. The data represent the average of the mean values obtained for three different osteoblast specimen. Error bars, SDs from the mean values.

Figure 6:
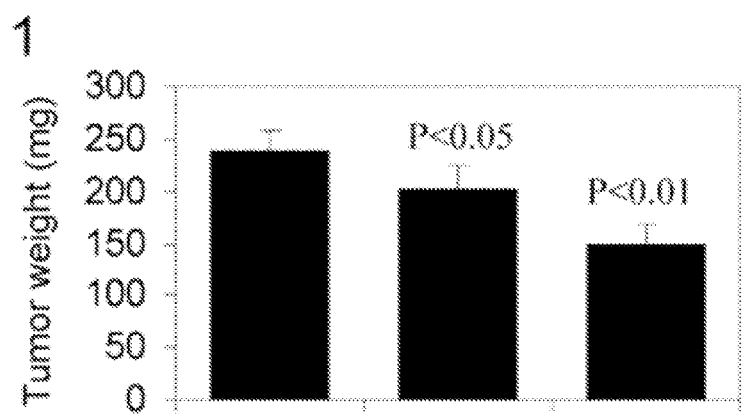
Figure 6:
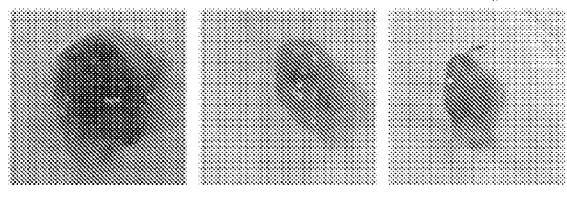
Figure 6:
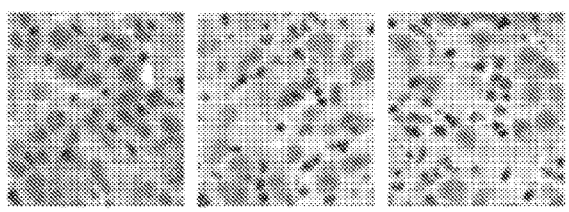

FIG. 6—A) Effects of SI-83 on cell viability of five human osteosarcoma cell lines measured by MTT assay. Data are expressed as percentage values respecting to DMSO, used as vehicle. Cells were treated with different concentrations of compound for 48 h. Values are means±SEM of three independent experiments performed in triplicates. Error bars show the SDs from the mean values. B) Inhibition of SaOS-2 xenograft growth. 1) Twelve mice were inoculated s.c. with tumour cells and were divided in three groups, receiving daily oral administration of cremphor vehicle, of 50 mg/kg SI-83 or of 100 mg/kg SI-83. At the endpoint ($26^{th}$ day after cell injection) tumours were weighted and mean values (±SD) expressed in grams were recorded. P values according to Student's t test are indicated. 2) Exemplificative images of tumour excised from one mouse of each group at the endpoint. 3) Immunohistologic analysis of xenografts. Tumour tissue sections were stained for the presence of phosphospecific-Src [pY416]. Representative images of tumour tissues from control xenografts and from treated group are shown (magnification ×300). The brown staining indicates the presence of the antigen and nuclei are stained with hematoxylin.

Figure 7:
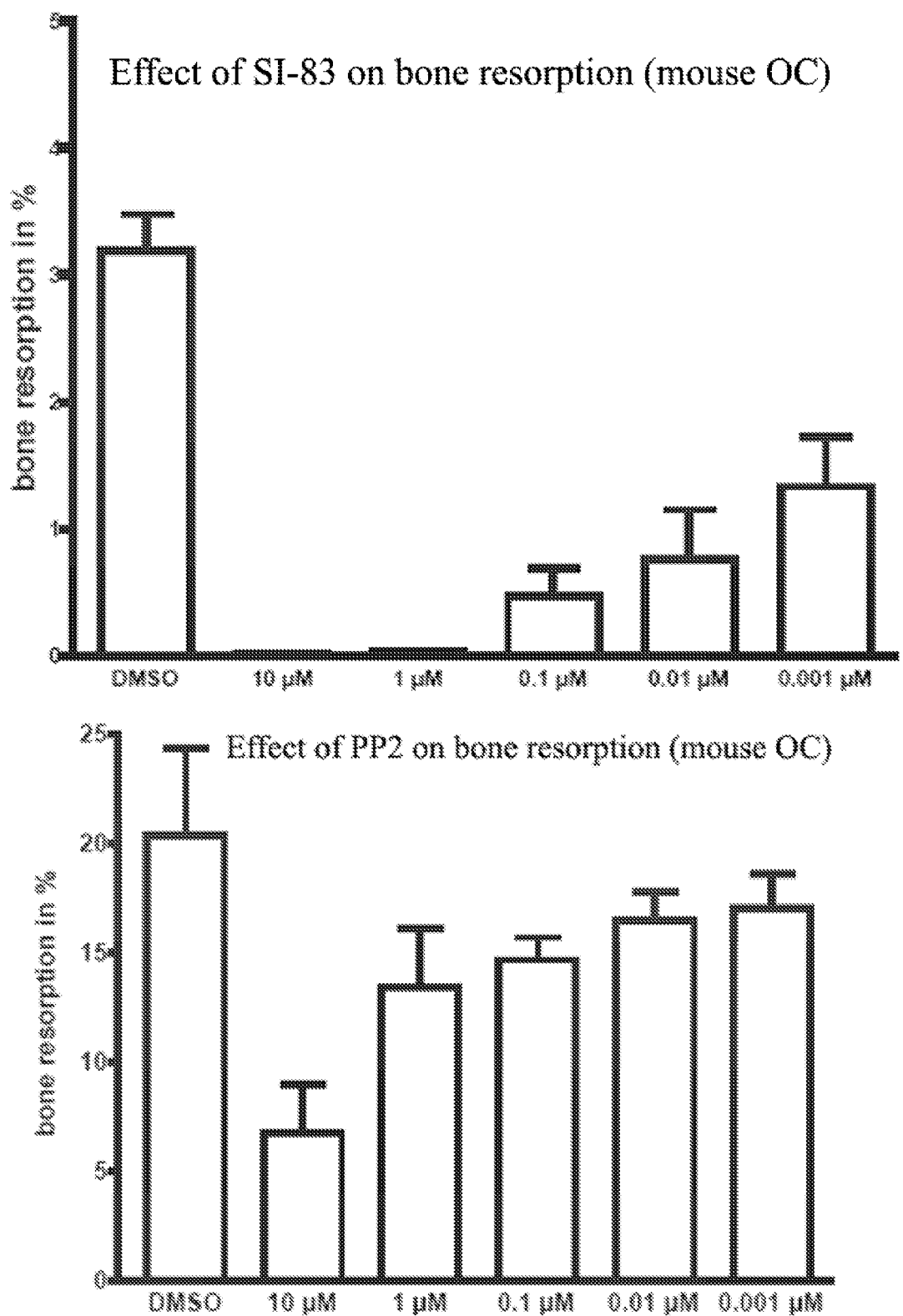
Figure 8A:
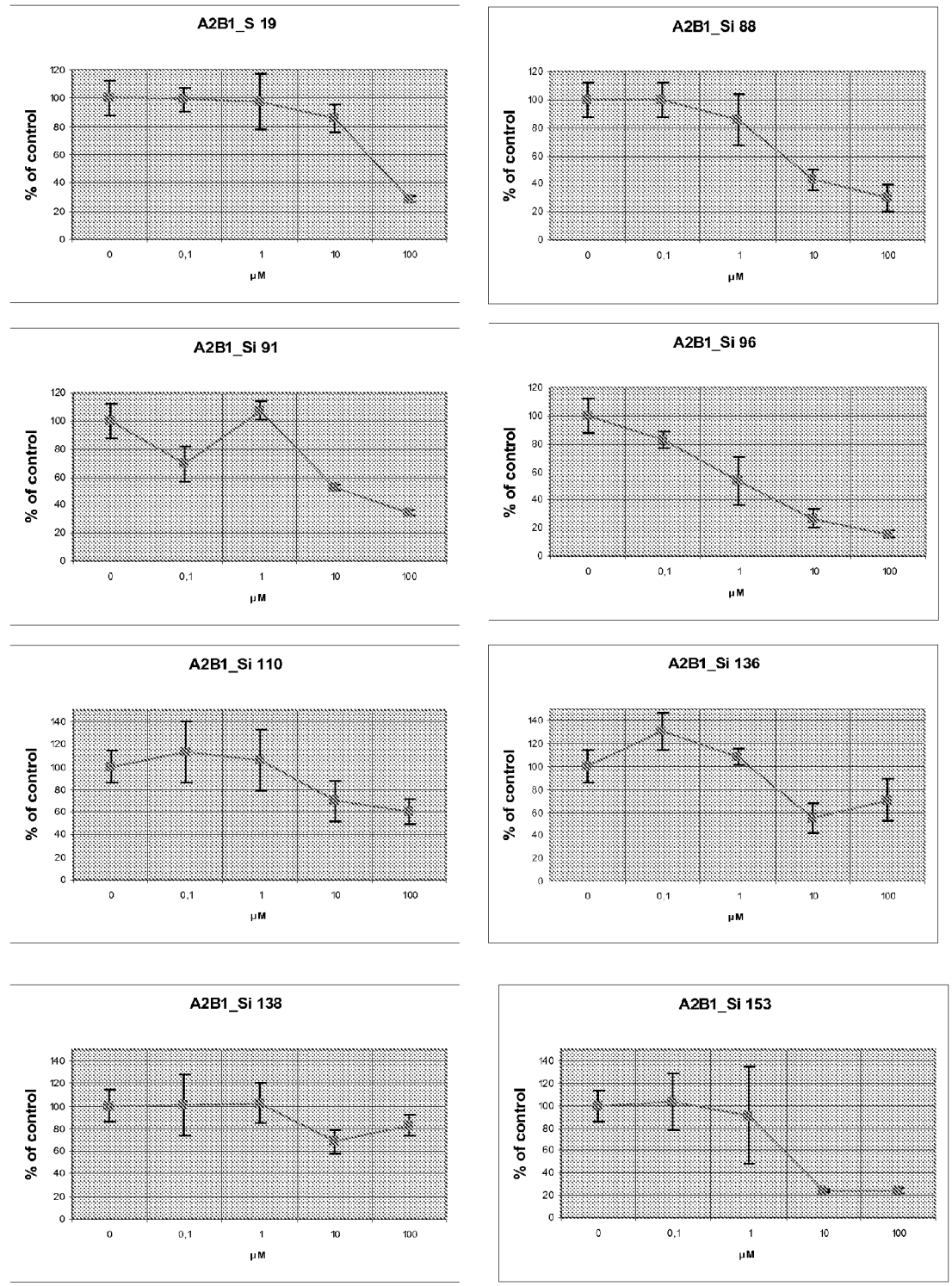
Figure 8B:
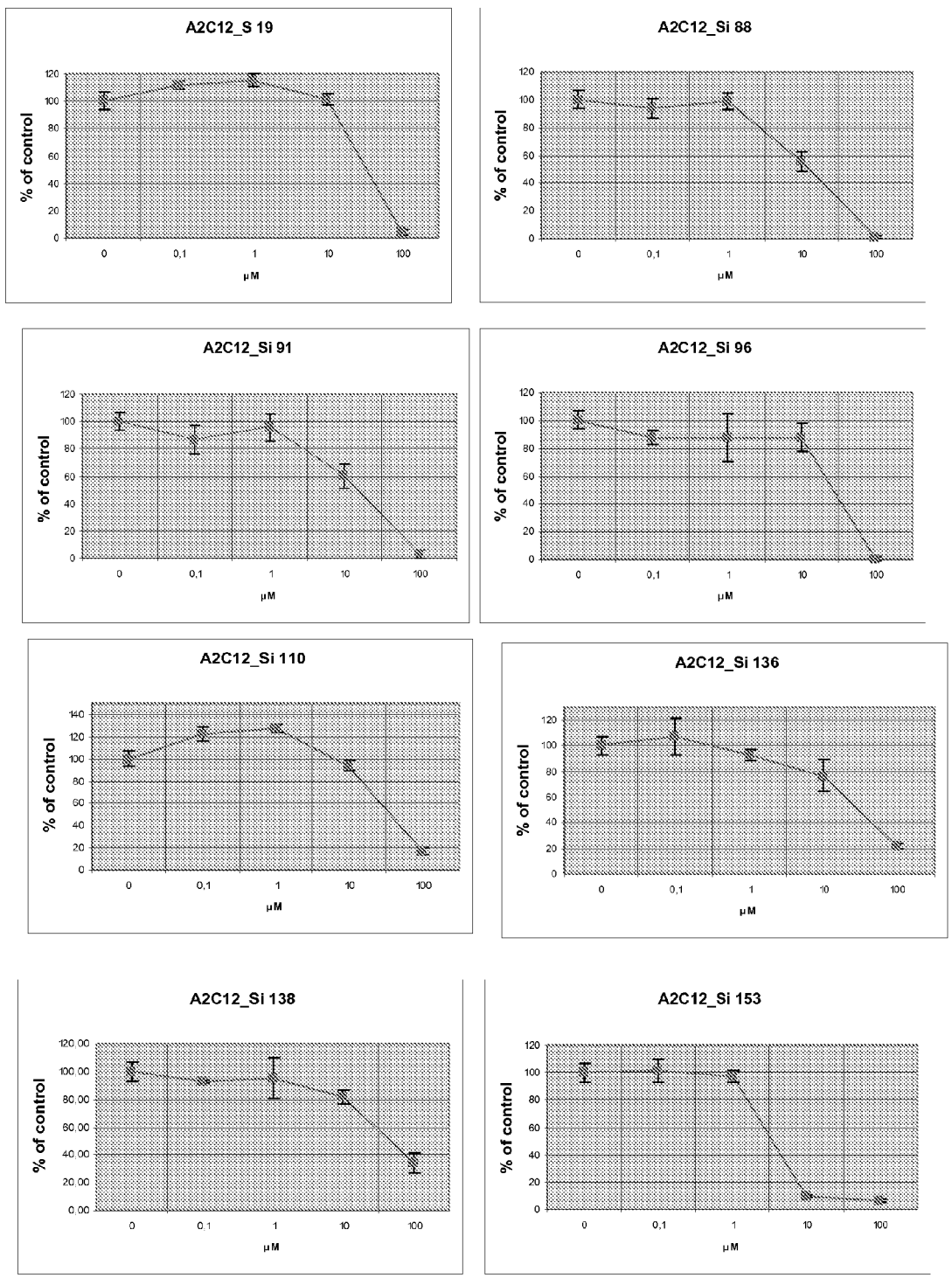
Figure 8C:
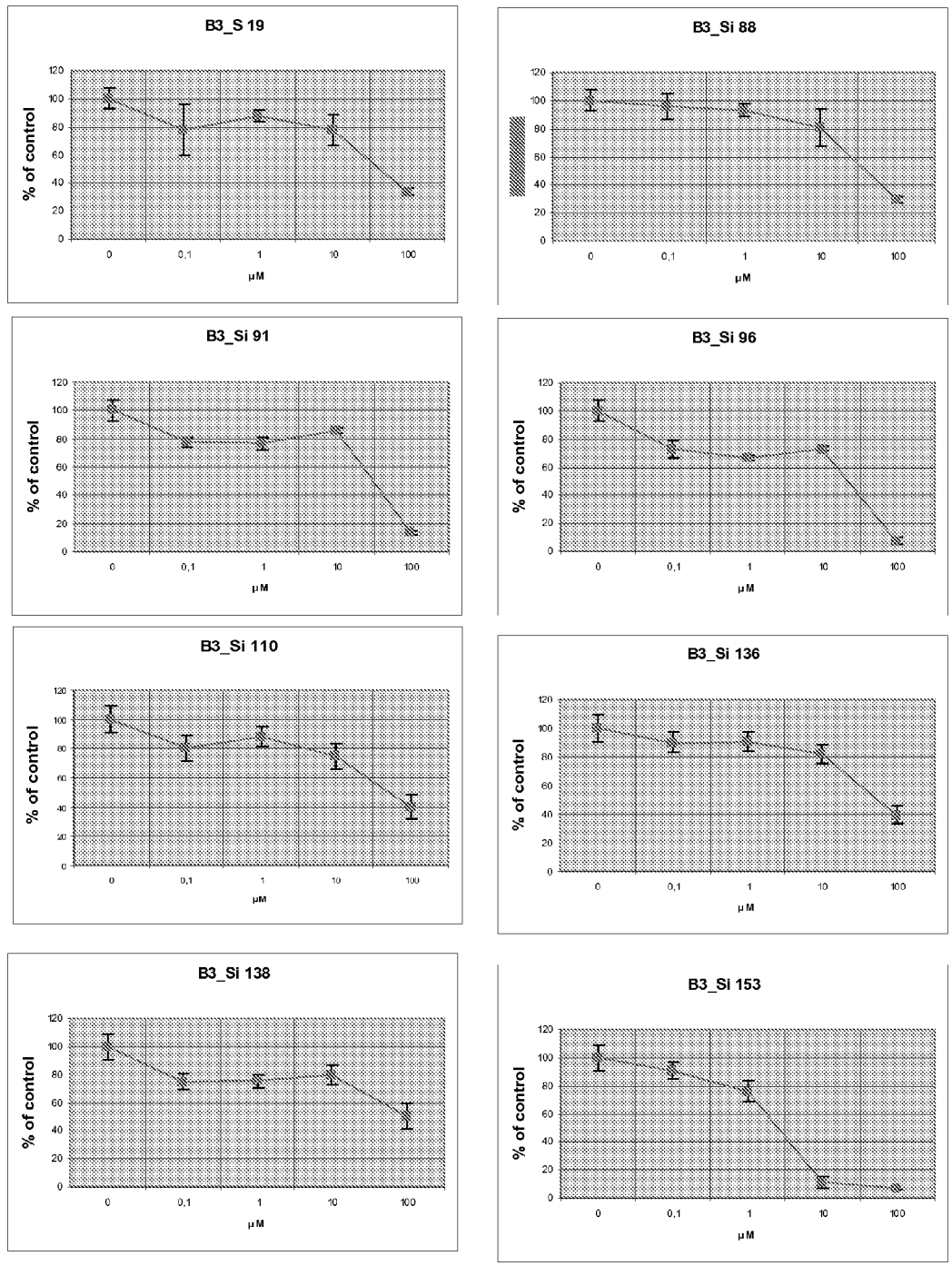
Figure 8D:
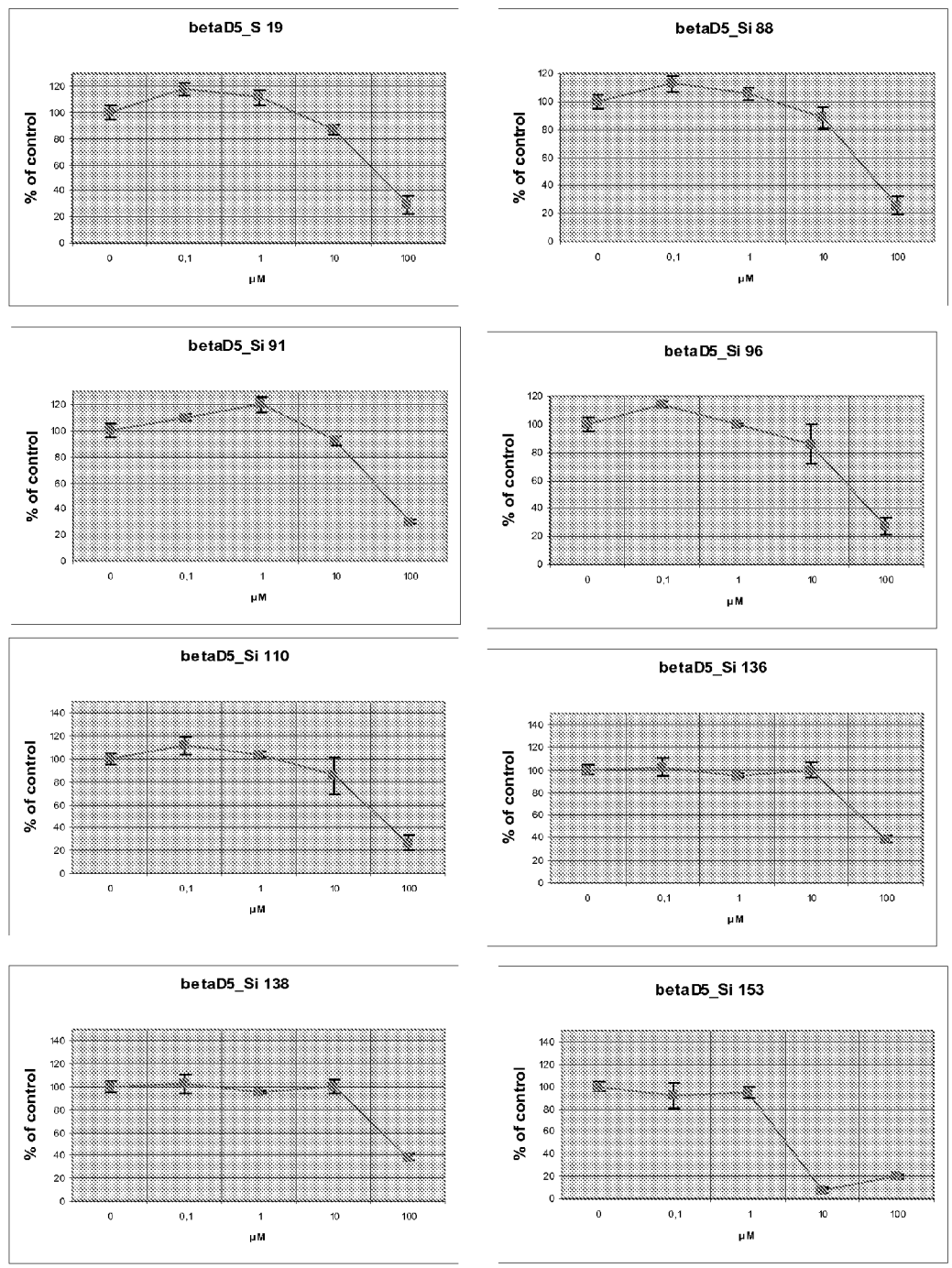
Figure 8E:
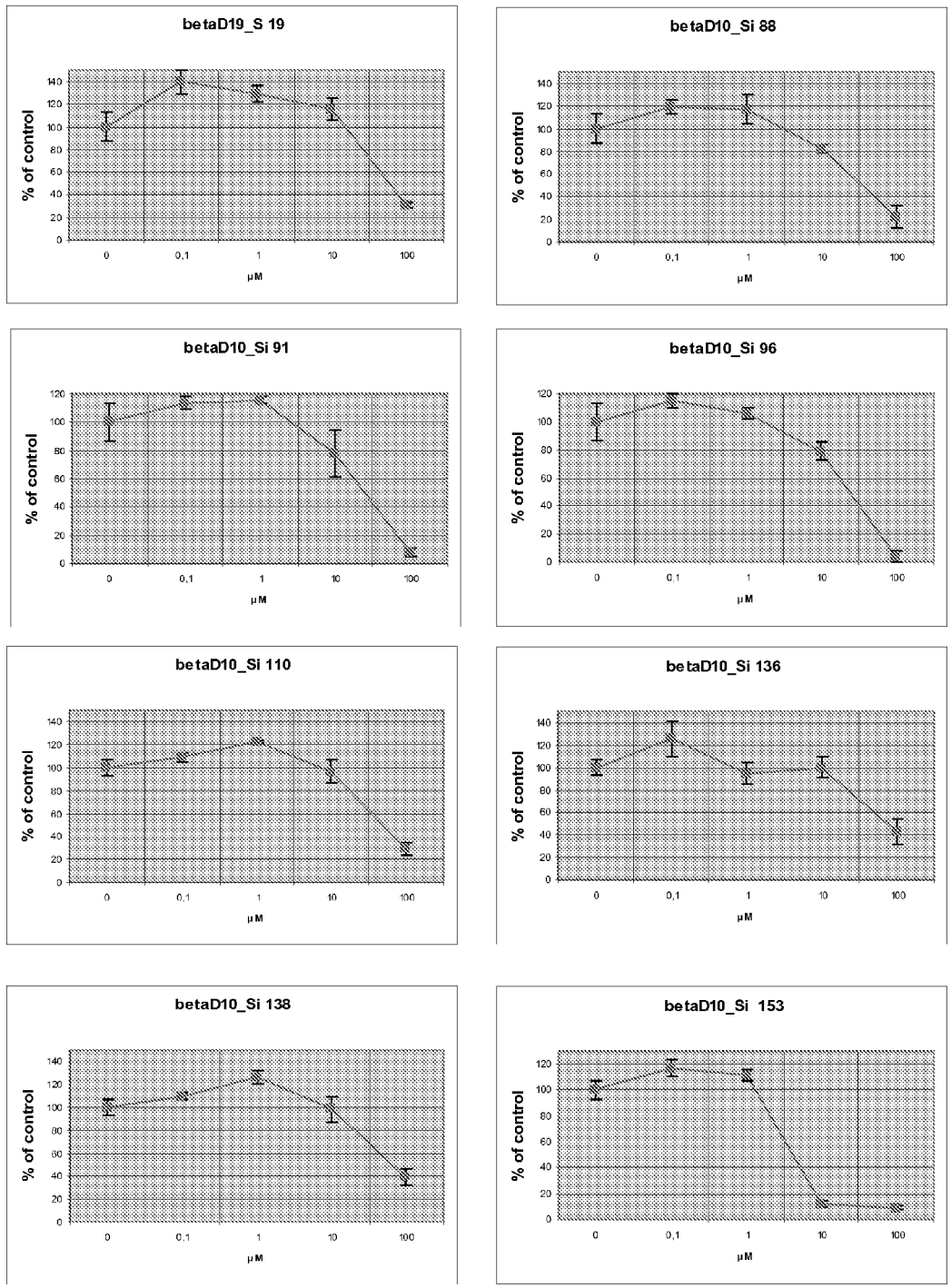
Figure 8F:
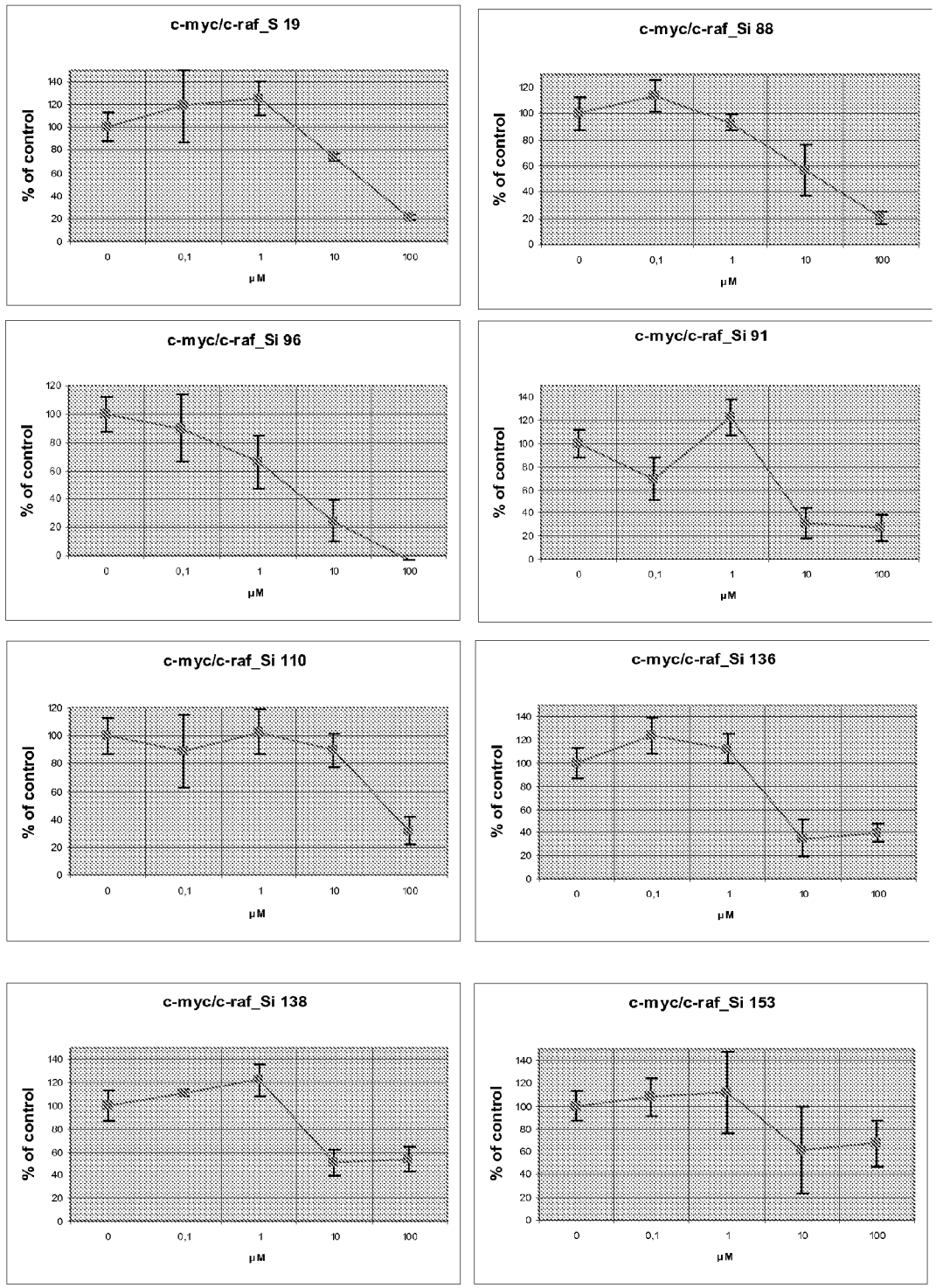
Figure 8G:
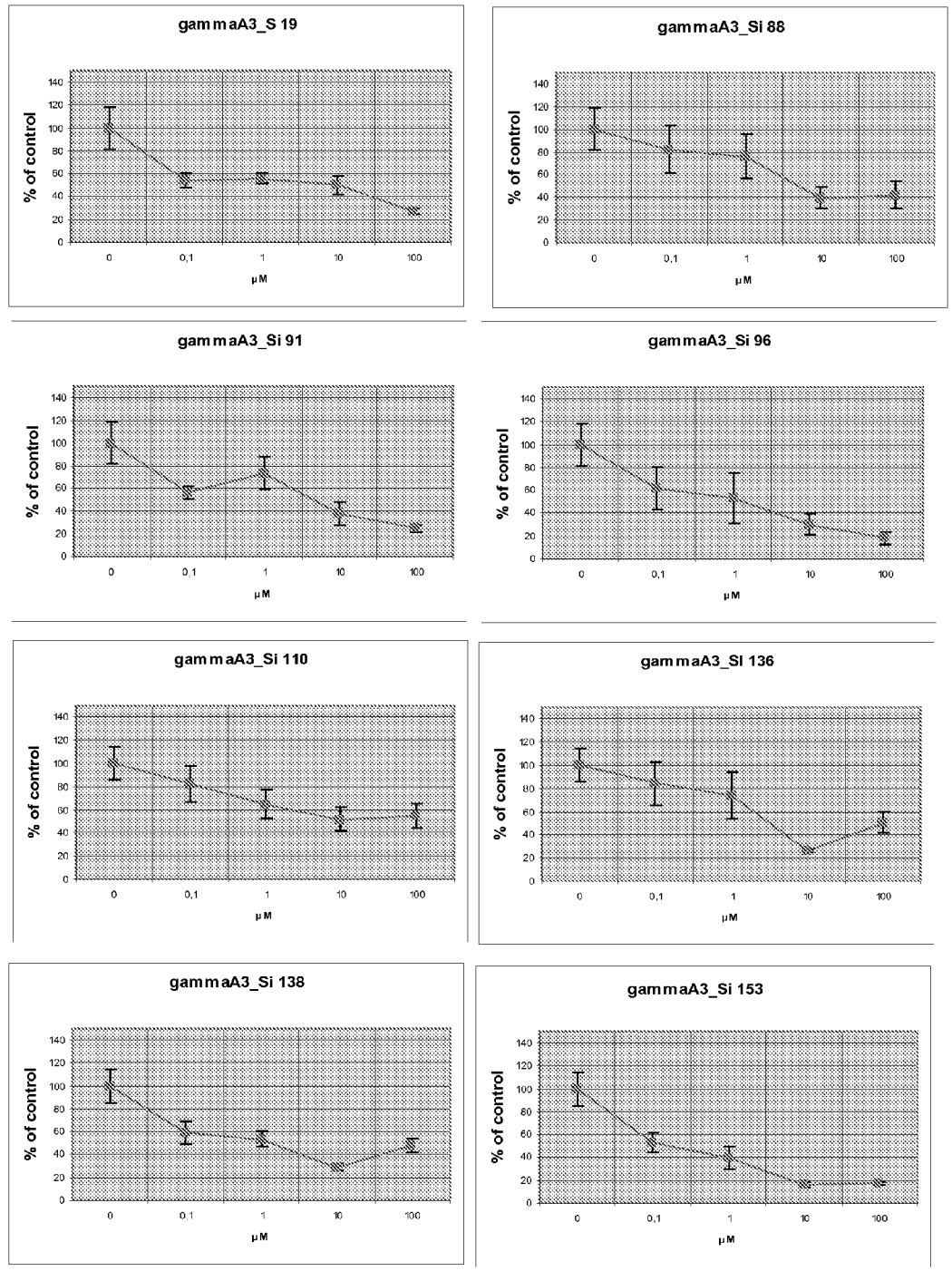
Figure 8H:
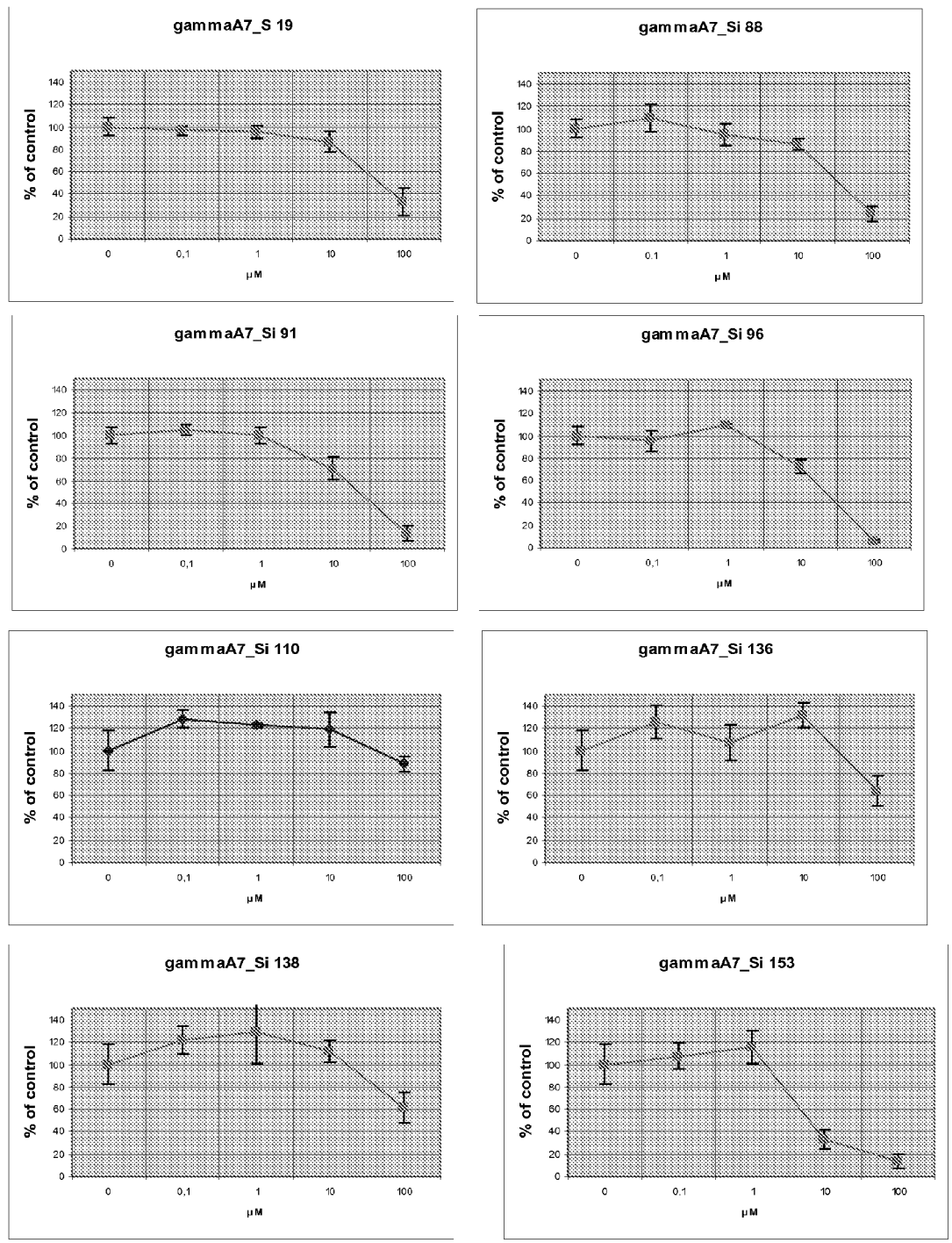
Figure 8I:
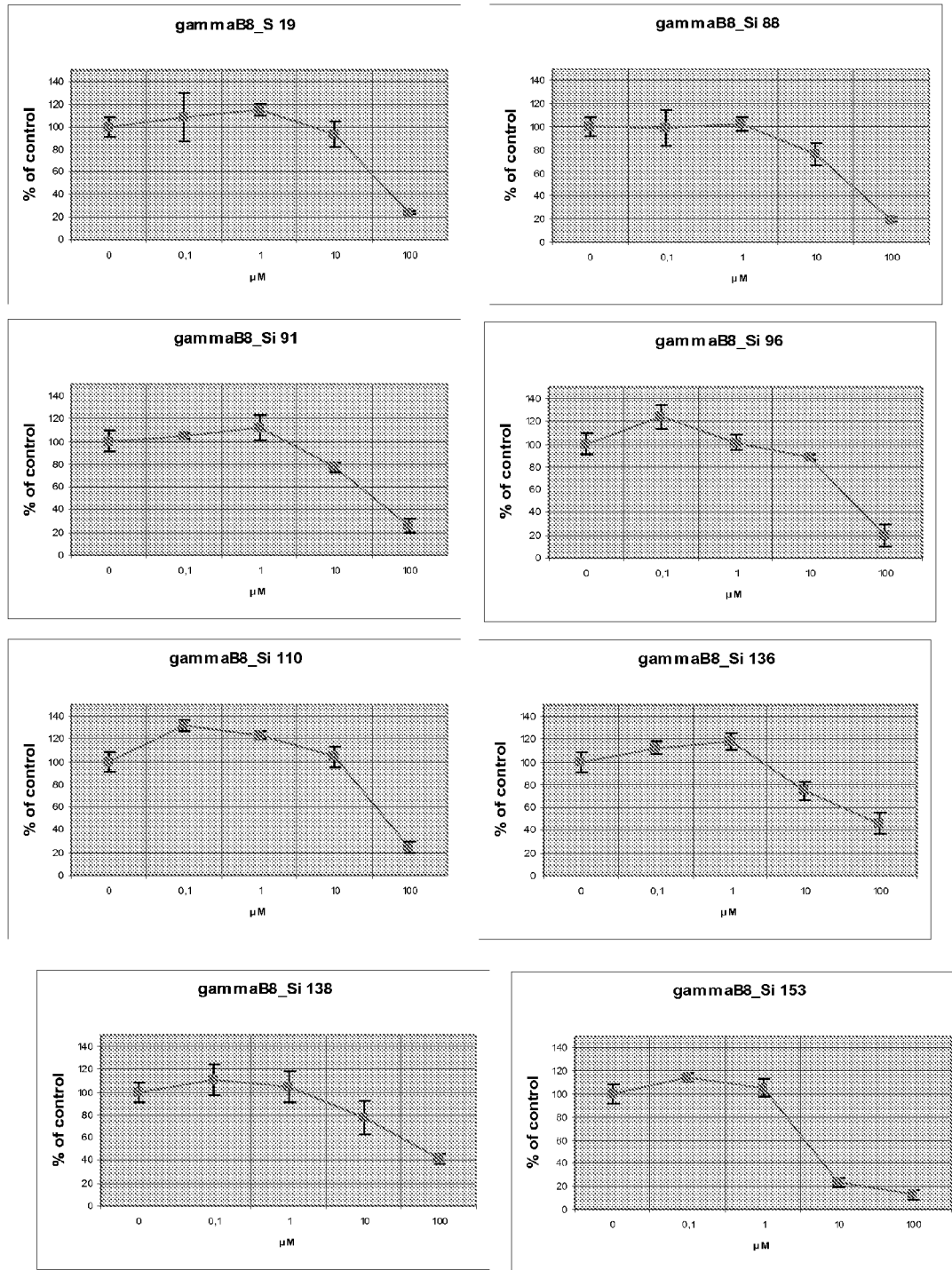
Figure 8J:
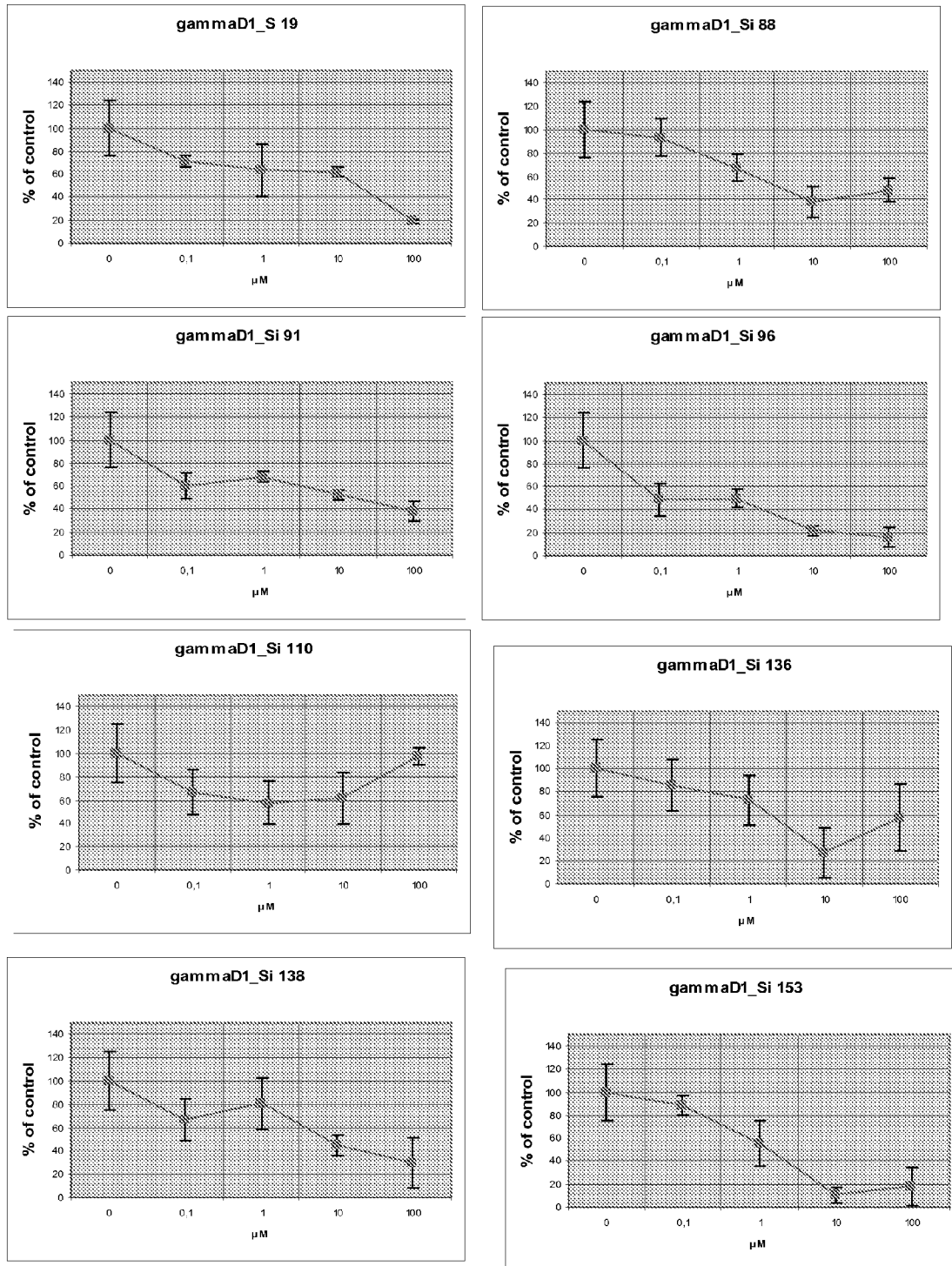
Figure 8K:
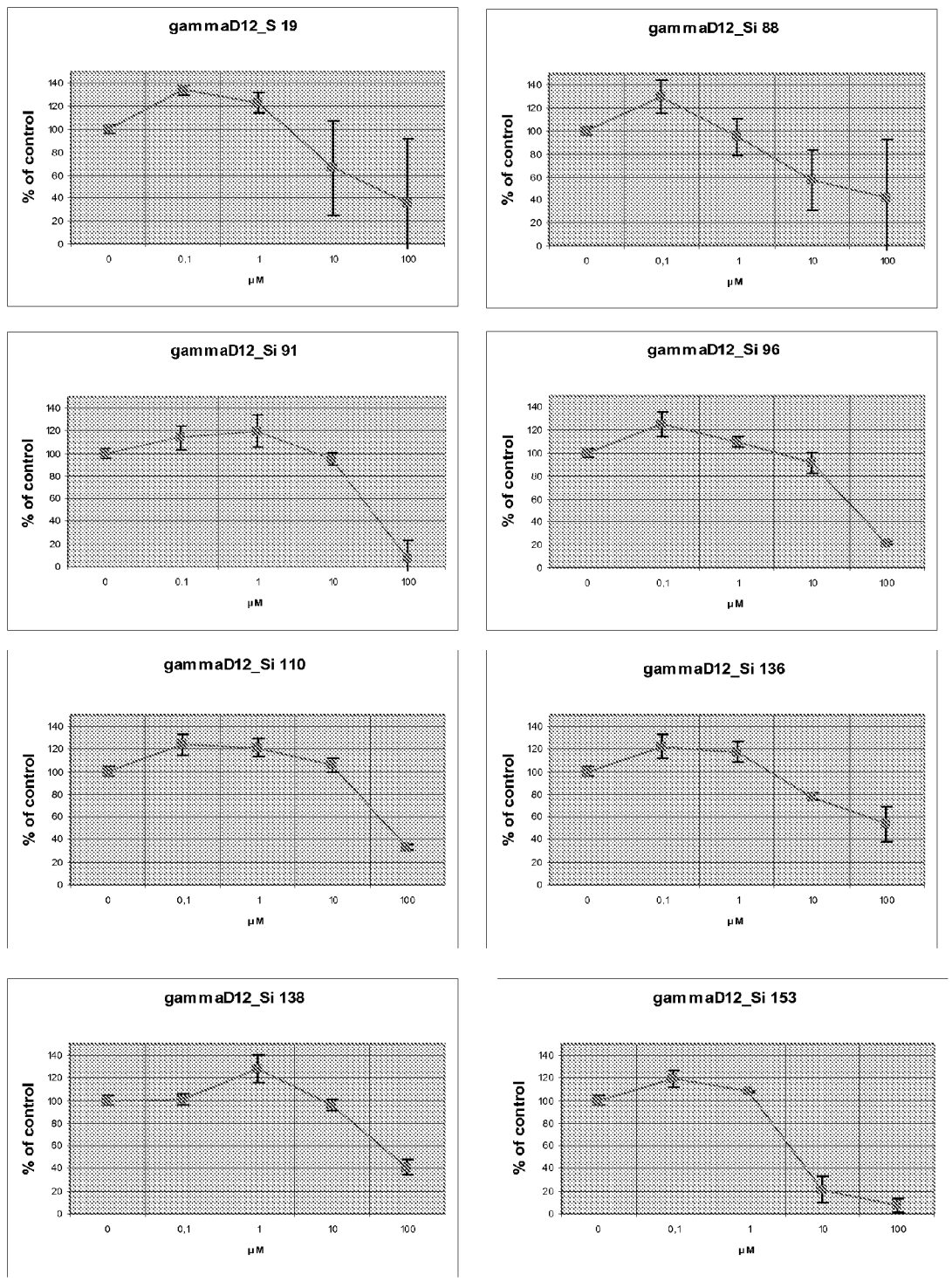

FIG. 7. Effect of SI-83 and PP2 on bone resorption (mouse osteoclasts).

FIG. 8. Graphical representation of growth inhibition induced by several new pyrazolo-pyrimidines (namely, S-19, SI-88, SI-91, SI-96, SI-110, SI-136, SI-138, and SI-153) on spontaneously-transformed tumor cells (A2B1, A2C12, B3, βD5, βD19, c-myc/c-raf, γA3, γA7, γB8, γD1, γD12) from mice.

Figure 9:
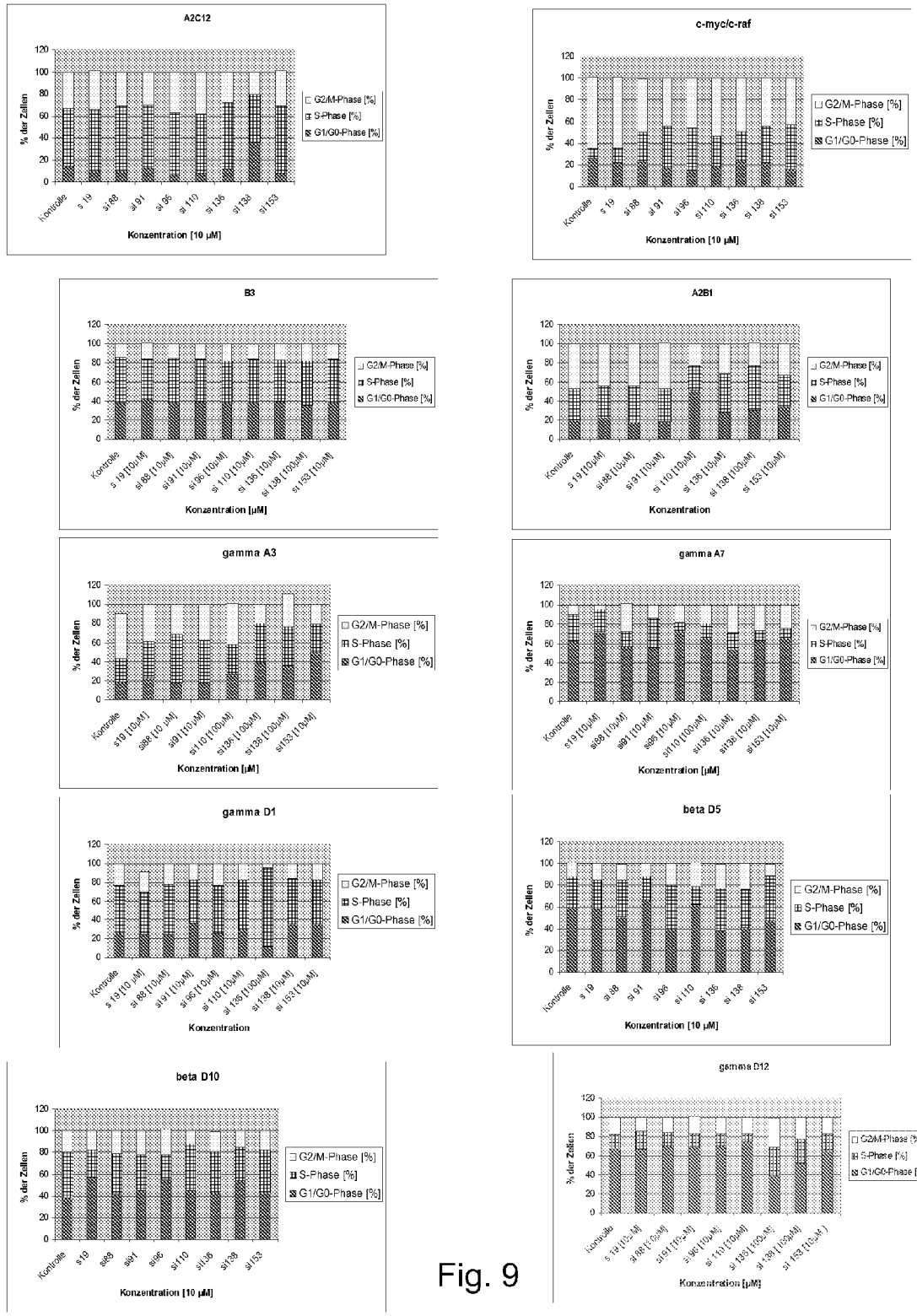

FIG. 9. Graphical representation of the influence of several new pyrazolo-pyrimidines (namely, S-19, SI-88, SI-91, SI-110, SI-136, SI-138, and SI-153) on the cell cycle of spontaneously-transformed tumor cells (A2B1, A2C12, B3, βD5, βD19, c-myc/c-raf, γA3, γA7, γB8, γD1, γD12) from mice.

EXAMPLE 1

Chemistry

Materials and Methods for Synthesis

Starting materials were purchased from Aldrich-Italia (Milan, Italy). Melting points were determined with a Büchi 530 apparatus and are uncorrected. IR spectra were measured in KBr with a Perkin-Elmer 398 spectrophotometer. $^1$H NMR spectra were recorded in a $(CD_3)_2SO$ solution on a Varian Gemini 200 (200 MHz) instrument. Chemical shifts are reported as δ (ppm) relative to TMS as internal standard, J in Hz. $^1$H patterns are described using the following abbreviations: s=singlet, d=doublet, t=triplet, q=quartet, sx=sextect, m=multiplet, br=broad.

All compounds were tested for purity by TLC (Merk, Silica gel 60 $F_{254}$, $CHCl_3$ as the eluant).

Analyses for C, H, N were within ±0.3% of the theoretical value.

Mass spectral (MS) data were obtained using an Agilent 1100 LC/MSD VL system (G1946C) with a 0.4 mL/min flow rate using a binary solvent system of 95:5 methyl alcohol/water. UV detection was monitored at 254 nm. Mass spectra were acquired in positive mode scanning over the mass range of 50-1500. The following ion source parameters were used: drying gas flow, 9 mL/min; nebulizer pressure, 40 psig; drying gas temperature, 350° C.

Synthesis and experimental data of compounds 26a, 27a, 28a, 29a, 30a, 30d, 31a, 31d, 32 were already reported by the authors.[18,22]

1-(4-Halophenyl)-2-hydrazinoethanols (26b,c). To hydrazine monohydrate (30 mL, 0.6 mol), heated at 100° C., the appropriate phenyloxirane (0.17 mmol) was added. The solution was heated for 30 min at 100° C. and the excess of hydrazine was removed under reduced pressure. The crude was purified by bulb to bulb distillation to obtain the pure products as pale yellow oils.

26b. Yield 85%, by 175-180° C. (0.6 mmHg). $^1$H NMR: δ 2.62-2.87 (m, 2H, $CH_2N$), 3.55-3.87 (m, 4H, $NH_2NH+OH$, disappears with $D_2O$), 4.85-4.92 (m, 1H, CHO), 6.95-7.29 (m, 4H Ar). IR $cm^{-1}$: 3323, 3280, 3250 ($NH_2+NH$), 3400-3000 (OH). Anal. ($C_8H_{11}N_2FO$) C, H, N.

26c. Yield 80%, by 170-175° C. (0.6 mmHg). $^1$H NMR: δ 2.65-2.88 (m, 2H, $CH_2N$), 3.56-3.90 (m, 4H, $NH_2NH+OH$, disappears with $D_2O$), 4.88-4.92 (m, 1H, CHO), 7.00-7.32 (m, 4H Ar). IR $cm^{-1}$: 3320, 3290, 3250 ($NH_2+NH$), 3350-2950 (OH). Anal. ($C_8H_{11}N_2ClO$) C, H, N.

Ethyl 5-amino-1-[2-(4-halophenyl)-2-hydroxyethyl]-1H-pyrazole-4-carboxylates (27b,c). The starting hydrazine 26b or 26c (20 mmol) was added to a solution of ethyl(ethoxymethylene)cyanoacetate (3.38 g, 20 mmol) in anhydrous toluene (20 mL) and the mixture was heated at 80° C. for 8 h. The solution was then concentrated under reduced pressure to half of the volume and allowed to cool to room temperature. The yellow pale solids were filtered and recrystallized from toluene to afford 27b and 27c as white solids.

27b. Yield 70%, mp 163-164° C. $^1$H NMR: δ 1.33 (t, J=7.0, 3H, $CH_3$), 3.73 (br s, 1H, OH, disappears with $D_2O$), 3.90-4.15 (m, 2H, $CH_2N$), 4.29 (q, J=7.0, 2H, $CH_2O$), 5.01-5.18

(m, 1H, CHO), 5.36 (br s, 2H, $NH_2$, disappears with $D_2O$), 7.03-7.40 (2m, 4H Ar), 7.55 (s, 1H, H-3). IR $cm^{-1}$: 3448, 3346 ($NH_2$), 3300-3000 (OH), 1685 (CO). Anal. ($C_{14}H_{16}N_3FO_3$) C, H, N.

27c. Yield 75%, mp 168-169° C. $^1$H NMR: δ 1.38 (t, J=7.0, 3H, $CH_3$), 3.56 (br s, 1H, OH, disappears with $D_2O$), 3.91-4.19 (m, 2H, $CH_2N$), 4.28 (q, J=7.0, 2H, $CH_2O$), 5.05-5.18 (m, 1H, CHO), 5.33 (br s, 2H, $NH_2$, disappears with $D_2O$), 7.25-7.46 (m, 4H Ar), 7.59 (s, 1H, H-3). IR $cm^{-1}$: 3412, 3291 ($NH_2$), 3219-3100 (OH), 1689 (CO). Anal. ($C_{14}H_{16}N_3ClO_3$) C, H, N.

Ethyl 5-{[(benzoylamino)carbonothioyl]amino}-1-[2-(4-halophenyl)-2-hydroxyethyl]-1H-pyrazole-4-carboxylates (28b,c). A suspension of 27b or 27c (10 mmol) and benzoyl isothiocyanate (1.7 g, 11 mmol) in anhydrous THF (20 mL) was refluxed for 12 h. The solvent was evaporated under reduced pressure and 28b was crystallized adding diethyl ether (30 mL) as a white solid, while 28c was used as crude oil for the next reaction.

28b. Yield 85%, mp 129-130° C. $^1$H NMR: δ 1.31 (t, J=7.0, 3H, $CH_3$), 4.10-4.38 (m, 5H, $2CH_2$+OH, 1H disappears with $D_2O$), 5.25-5.38 (m, 1H, CHO), 7.00-7.90 (m, 9H Ar), 8.05 (s, 1H, H-3), 9.36 (s, 1H, NH, disappears with $D_2O$), 12.16 (s, 1H, NH, disappears with $D_2O$). IR $cm^{-1}$: 3444, 3261 (NH), 3190-2940 (OH), 1683 (CO). Anal. ($C_{22}H_{21}N_4FO_4S$) C, H, N, S.

1-[2-(4-Halophenyl)-2-hydroxyethyl]-6-thioxo-1,5,6,7-tetrahydro-4H-pyrazolo[3,4-d]pyrimidin-4-ones (29b,c). A solution of 28b or 28c (10 mmol) in 2M NaOH (40 mL) was refluxed for 10 min and then diluted with $H_2O$ (40 mL) and acidified with glacial acetic acid. Standing in a refrigerator for 12 h, a solid crystallized that was filtered and recrystallized from absolute ethanol to give 29b and 29c as white solids.

29b. Yield 75%, mp 252-253° C. $^1$H NMR: δ 4.15-4.28 and 4.52-4.60 (2m, 2H, $CH_2N$), 4.88-5.00 (m, 1H, CHO), 5.69 (s, 1H, OH, disappears with $D_2O$), 7.12-7.29 and 7.40-7.52 (2m, 4H Ar), 7.98 (s, 1H, H-3), 12.20 (s, 1H, NH, disappears with $D_2O$), 13.36 (s, 1H, NH, disappears with $D_2O$). IR $cm^{-1}$: 3315, 3200 (NH), 3320-2500 (OH), 1670 (CO). Anal. ($C_{13}H_{11}N_4FO_2S$) C, H, N, S.

29c. Yield 70%, mp 249-250° C. $^1$H NMR: δ 4.13-4.65 (2m, 2H, $CH_2N$), 4.84-5.00 (m, 1H, CHO), 5.71 (br s, 1H, OH, disappears with $D_2O$), 7.30-7.51 (m, 4H Ar), 7.97 (s, 1H, H-3), 12.19 (s, 1H, NH, disappears with $D_2O$), 13.38 (s, 1H, NH, disappears with $D_2O$). IR $cm^{-1}$: 3390, 3220 (NH), 3100-2700 (OH), 1675 (CO). Anal. ($C_{13}H_{11}N_4ClO_2S$) C, H, N, S.

1-Substituted-6-(alkyl)thio)-1,5-dihydro-4H-pyrazolo[3,4-d]pyrimidin-4-ones (30b,c,e). A solution of 29a-c (10 mmol) and the appropriate alkyl iodide (50 mmol) in anhydrous THF (20 mL) was refluxed for 12 h. The solvent and the excess of alkyl iodide were removed by distillation under reduced pressure. The residue oil was crystallized by adding $CHCl_3$ (10 mL) and was purified by recrystallization with absolute ethanol to give 30b,c as white solids. Compound 30e was purified by column chromatography (Silica Gel), using a mixture of $CHCl_3$:$CH_3OH$ (8:2) as eluant.

30b. Yield 72%, mp 217-218° C. $^1$H NMR: δ 2.51 (s, 3H, $CH_3S$), 4.24-4.50 (m, 2H, $CH_2N$), 4.55 (br s, 1H, OH, disappears with $D_2O$), 5.00-5.15 (m, 1H, CHO), 7.02-7.30 (m, 4H Ar), 7.96 (s, 1H, H-3), 12.33 (s, 1H, NH, disappears with $D_2O$). IR $cm^{-1}$: 3418 (NH), 3120-2850 (OH), 1668 (CO). Anal. ($C_{14}H_{13}N_4FO_2S$) C, H, N, S.

30c. Yield 70%, mp 210-211° C. $^1$H NMR: δ 2.84 (s, 3H, $CH_3S$), 4.22-4.48 (m, 2H, $CH_2N$), 4.94-5.16 (m, 1H, CHO), 5.76 (d, 1H, OH, disappears with $D_2O$), 7.07-7.22 (m, 4H Ar), 7.94 (s, 1H, H-3), 12.32 (s, 1H, NH, disappears with $D_2O$). IR $cm^{-1}$: 3427 (NH), 3120-2850 (OH), 1667 (CO). Anal. ($C_{14}H_{13}N_4ClO_2S$) C, H, N, S.

30e. Yield 68%, mp 165-166° C. $^1$H NMR: δ 0.91 (t, J=7.2, 3H, $CH_3$), 1.61 (sext, J=7.2, 2H, $CH_3CH_2$), 3.01 (t, J=7.2, 2H, $CH_2S$), 4.14-4.38 (m, 2H, $CH_2N$), 4.92-5.05 (m, 1H, CHO), 5.76 (d, 1H, OH, disappears with $D_2O$), 7.08-7.18 (m, 5H Ar), 7.87 (s, 1H, H-3), 12.20 (br s, 1H, NH, disappears with $D_2O$). IR $cm^{-1}$: 3346 (NH), 3130-2900 (OH), 1692 (CO). Anal. ($C_{16}H_{18}N_4O_2S$) C, H, N, S.

1-Substituted-[4-chloro-6-(alkylthio)-1H-pyrazolo[3,4-d]pyrimidines (31b,c,e). The Vilsmeier complex, previously prepared from $POCl_3$ (6.13 g, 40 mmol) and anhydrous DMF (2.92 g, 40 mmol) was added to a suspension of 30b,c,e (10 mmol) in $CHCl_3$ (20 mL) and the mixture was refluxed for 4 h. The solution was washed with $H_2O$ (2×20 mL), dried ($MgSO_4$), filtered and concentrated under reduced pressure. The crude oil was purified by column chromatography (Florisil® 100-200 mesh), using diethyl ether as the eluant, to afford the pure product 31b,c,e as white solids.

31b. Yield 70%, mp 136-137° C. $^1$H NMR: δ 2.65 (s, 3H, $CH_3S$), 4.74-5.03 (m, 2H, $CH_2N$), 5.42-5.54 (m, 1H, CHCl), 6.96-7.08 and 7.29-7.44 (2m, 4H Ar), 8.03 (s, 1H, H-3). Anal. ($C_{14}H_{11}N_4Cl_2F S$) C, H, N, S.

31c. Yield 60%, mp 142-143° C. $^1$H NMR: b. 2.65 (s, 3H, $CH_3S$), 4.74-5.03 (m, 2H, $CH_2N$), 5.42-5.53 (m, 1H, CHCl), 7.25-7.42 (m, 4H Ar), 8.03 (s, 1H, H-3). Anal. ($C_{14}H_{11}N_4Cl_3S$) C, H, N, S.

31e. Yield 65%, mp 83-84° C. $^1$H NMR: δ 1.05 (t, J=7.2, 3H, $CH_3$), 1.77 (sext, J=7.2, 2H, $CH_3CH_2$), 3.11 (t, J=7.2, 2H, $CH_2S$), 4.64-4.95 (m, 2H, $CH_2N$), 5.32-5.46 (m, 1H, CHCl), 7.07-7.38 (m, 5H Ar), 7.95 (s, 1H, H-3). Anal. ($C_{16}H_{16}N_4Cl_2S$) C, H, N, S.

General procedure for the 4-amino-1H-pyrazolo[3,4-d]pyrimidines (SI56-61, SI-65, SI70-72, SI84-88). To a solution of 31a, 31b, 31c or 31d (5 mmol) in anhydrous toluene (20 mL), the proper amine (20 mmol) was added. The reaction mixture was stirred at room temperature for 36 h and then extracted with $H_2O$ (2×20 mL). The organic phase was dried ($MgSO_4$), filtered and concentrated under reduced pressure. The oil residue was crystallized by adding diethyl ether (10 mL) to give the final products as white solids.

2. Yield 73%, mp 111-112° C. $^1$H NMR: δ 2.49 (s, 3H, $CH_3S$), 2.89 (t, J=7.0, 2H, $CH_2Ar$), 3.75 (q, J=7.0, 2H, $CH_7NH$), 4.58-4.90 (m, 2H, $CH_2N$), 5.14 (br s, 1H, NH, disappears with $D_2O$), 5.34-5.51 (m, 1H, CHCl), 6.77-7.43 (m, 9H Ar), 7.64 (s, 1H, H-3). IR $cm^{-1}$: 3248 (NH). MS (ESI) m/z 444.2 $[M+H]^+$; 464.2 $[M+Na]^+$. Anal. ($C_{22}H_{21}N_5ClFS$) C, H, N, S.

General procedure for the 4-anilino-1H-pyrazolo[3,4-d]pyrimidines (SI-83, SI-90, SI-91, SI-96, SI-118, SI-128). To a solution of 31a, 31b, 31d and 31e (5 mmol) in absolute ethanol (20 mL), the appropriate aniline (5 mmol) was added and the reaction mixture was stirred at reflux for 3 h. After cooling, a solid precipitated that was filtered, washed with $H_2O$ and recrystallized from absolute ethanol (10 mL) to give the final products as white solids. Compound 24 was prepared with the same procedure starting from 32.

18. Yield 55%, mp 102-103° C. $^1$H NMR: δ 2.52 (s, 3H, $CH_3S$), 4.58-4.90 (m, 2H, $CH_2N$), 5.34-5.44 (m, 1H, CHCl), 7.08-7.36 (m, 9H Ar), 7.57 (s, 1H, H-3). IR $cm^{-1}$: 3277 (NH). MS (ESI) m/z 430.2 $[M+H]^+$; 452.2 [M+Na] Anal. ($C_{20}H_{17}N_5Cl_2S$) C, H, N, S.

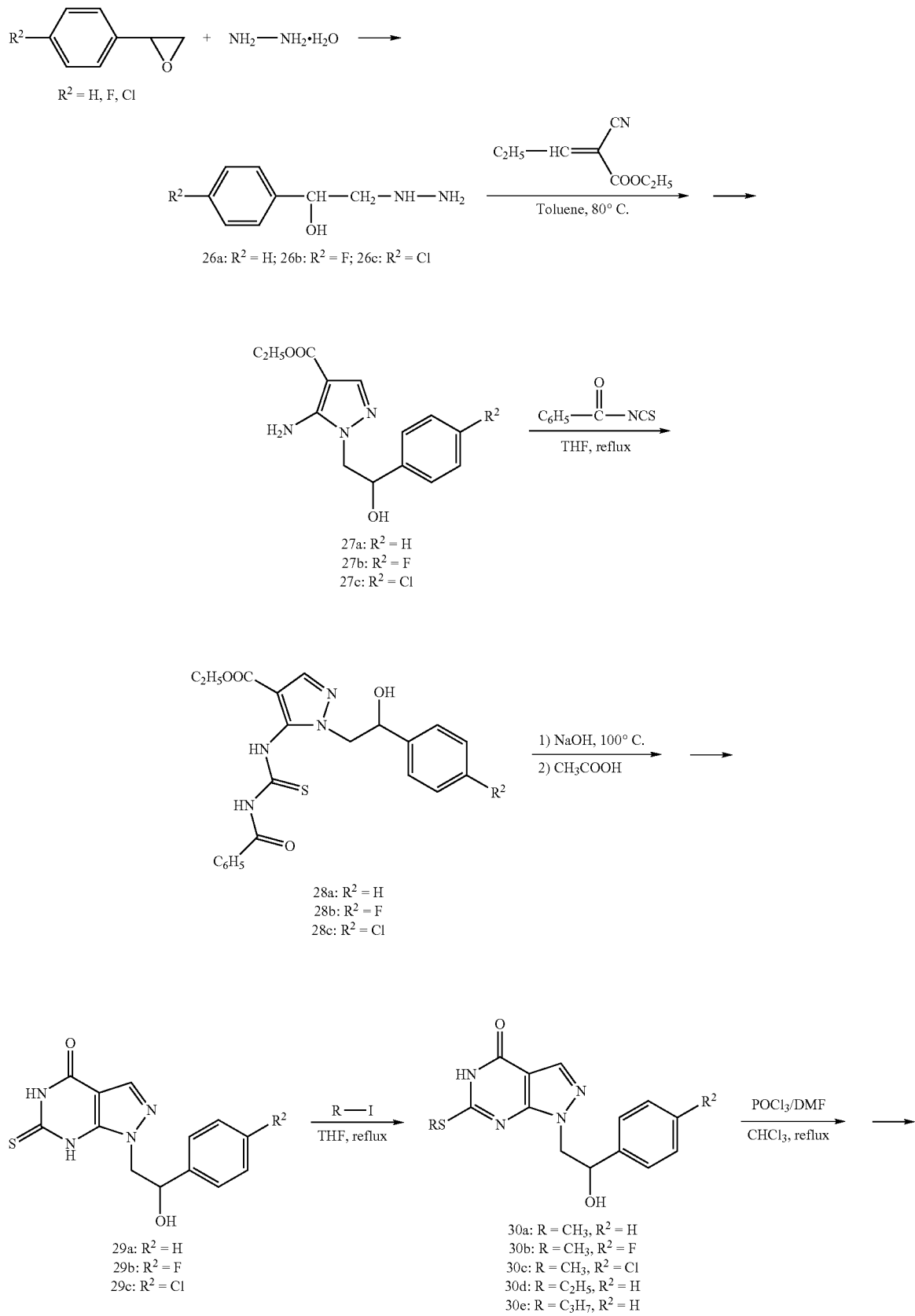

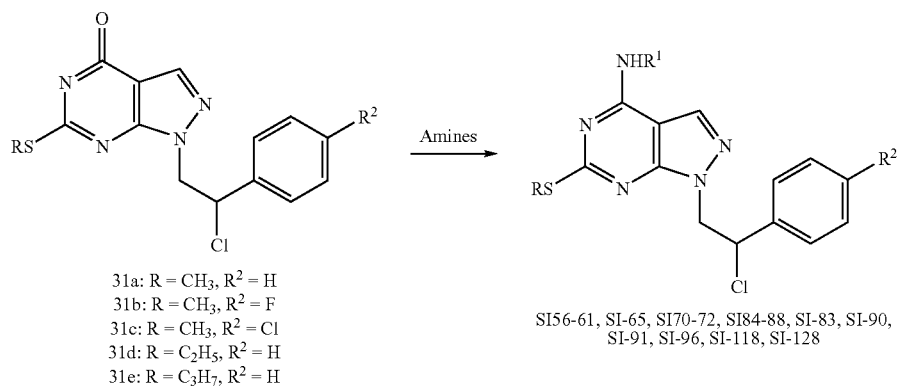

31a: R = CH$_3$, R$^2$ = H
31b: R = CH$_3$, R$^2$ = F
31c: R = CH$_3$, R$^2$ = Cl
31d: R = C$_2$H$_5$, R$^2$ = H
31e: R = C$_3$H$_7$, R$^2$ = H

SI56-61, SI-65, SI70-72, SI84-88, SI-83, SI-90,
SI-91, SI-96, SI-118, SI-128

EXAMPLE 2

Biological Activity

Assays on Ba/F3 Cells

The results of enzymatic cell-free assays proved that such molecules inhibit non-receptor tyrosine kinase activities, in particular Abl and Src, at IC$_{50}$ doses ranging from 0.08 and 0.8 μM. In particular, to asses the potency of one of these molecules, namely S29, the authors tried its cytotoxic effects on Bcr-Abl-transduced cell lines (BaF3) either sensitive or resistant to Imatinib. Imatinib resistance was provided by mutations at functionally distinct regions of the Bcr-Abl kinase domain, including the P-loop (Y253F and E255K) and T315I, and spontaneous selection in presence of Imatinib with or without growth factor (IL-3) additioned to culture media not due to Bcr-Abl amplification or mutations. Ba/F3 cells expressing wt and mutated Bcr-Abl constructs have been donated by M. W. Deininger (Center for Hematologic Malignancies, Oregon Health and Sciences University). Details on site-directed mutagenesis used to generate IM-resistant Bcr-Abl constructs have been provided in a previously published paper.[56] Apoptosis induction has been evaluated at 24$^{th}$ and 48$^{th}$ exposure to 1 μM IM and 5 μM of S29.

Drug anti-proliferative effects have been assayed in clonogenic assays (0.9% methylcellulose additioned with 30% FCS). Cellular cultures were kept in the presence of 5% CO2 for 10 days at 37° C. To evaluate the cellular sensitivity to S29, cells were treated for 10 days with S29 scalar doses ranging from 5 μM and 1 μM. Lethal dose 50 (LD$_{50}$) was calculated by logarithmic regression analysis. S29 significantly reduced proliferation in the semisolid assay of cell clones expressing the wt and mutated Bcr-Abl genes and LD$_{50}$ ranged between 1.0 and 1.3 μM in all cases. Moreover, it was highly effective against cells rendered Imatinib-resistant by IL-3 and those transducing the p185 Bcr-Abl protein, usually referred to as controls for Imatinib-resistance (LD$_{50}$ ranging between 0.2 and 0.3 μM).

Apoptotic assay was performed on 1×10$^6$ cells and apoptotic cells were recognized by cytofluorimetric analysis of fluorescinated Annexin V (Roche) and PI uptake. Cell fluorescence and PI uptake were measured by mean of a FACScan flow cytometer (set at 488 nm excitation and 530 nm bandpass filter wave length for fluorescin detection or >580 nm for PI detection) and a dedicated software (both from Beckton Dickinson). Interestingly, S29 induced apoptotic death on mutated cell lines after a 48 h treatment, while in IM-resistant cell lines additioned with IL-3 apoptosis occurred after 24 h of exposure.

The inhibitory effects of S29 toward the phosphorylation of Bcr-Abl (Tyr245), Src (Tyr416) and Lyn (Tyr507) were assessed using western blot analysis. Whole cell lysates were obtained from 1×10$^7$ cells (either untreated or following 24 h and 48 h exposure to 5 μM S29) in lysis buffer.

Protein lysates from whole cells were incubated overnight with the primary antibodies (anti-Abl phosphorylated at Tyr245, Cell Signaling; anti-Src phosphorylated at Tyr416, Cell Signaling; anti-Lyn phosphorylated at Tyr507, Cell Signaling; anti-Lyn, Biosource; anti-Beta-actin, Santa Cruz Biotechnology) and then 1 h at rt with the secondary antibodies (Amersham). Beta actin was used for protein loading control. Signal intensities from 3 repeated blots were quantified by a GS-700 Imagining densitometer (BioRad) equipped with a dedicated software (Molecular Analyst).

Complementary abrogation of Bcr-Abl and Lyn-Src kinase phosphorylation persisted up to 24$^{th}$ h of exposure to S29 drug at 5 μM concentration both in Imatinib-sensitive and resistant contexts.

Novel Pyrazolo[3,4-d]Pyrimidines Affect Cell Viability of SaOS-2

A set of new pyrazolo[3,4-d]pyrimidine derivatives (Table 1) were assayed to evaluate their potential inhibition of cell viability toward human osteosarcoma SaOS-2 cells.

TABLE 1

Structure, Physicochemical Properties and biological data of test compounds.

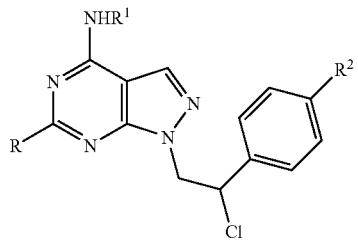

| Compd | R | R¹ | R² | mp | yield | $K_i^a$ | CV (%)$^b$ after 24 and 48 h |
|---|---|---|---|---|---|---|---|
| S-29 | H | p-F-C$_6$H$_4$CH$_2$ | Cl | | | 0.5 | ND |
| SI-56 | MeS | m-F-C$_6$H$_4$(CH$_2$)$_2$ | H | 111-112 | 73 | 13 | 101.1 ± 1.1; 100.8 ± 2.1 |
| SI-59 | MeS | o-Cl-C$_6$H$_4$(CH$_2$)$_2$ | H | 99-100 | 70 | 4.0 | 102.9 ± 1.3; 100.5 ± 0.5 |
| SI-58 | MeS | m-Cl-C$_6$H$_4$(CH$_2$)$_2$ | H | 122-123 | 68 | 6.0 | 80.6 ± 0.7; 39.3 ± 2.0 |
| SI-57 | MeS | p-Cl-C$_6$H$_4$(CH$_2$)$_2$ | H | 99-100 | 70 | 25 | 85.2 ± 0.7; 75.4 ± 1.3 |
| SI-60 | MeS | p-Me-C$_6$H$_4$(CH$_2$)$_2$ | H | 99-100 | 71 | 15 | 101.9 ± 1.9; 96.3 ± 1.1 |
| SI-61 | MeS | p-MeO-C$_6$H$_4$(CH$_2$)$_2$ | H | 60-61 | 62 | 4.0 | 101.0 ± 3.0; 49.8 ± 2.1 |
| SI-63 | MeS | C$_4$H$_9$ | F | | | 19 | 102.2 ± 2.5; 59.1 ± 1.9 |
| SI-68 | MeS | C$_4$H$_9$ | Cl | | | 1.5 | 99.7 ± 3.1; 93.6 ± 3.1 |
| SI-70 | MeS | CH$_2$C$_6$C$_5$ | Cl | | | 3.0 | 52.2 ± 2.4; 24.4 ± 2.5 |
| SI-71 | MeS | C$_6$C$_5$(CH$_2$)$_2$ | Cl | 127-129 | 71 | 2.8 | 99.9 ± 0.9; 89.4 ± 2.3 |
| S1-72 | EtS | C$_6$C$_5$(CH$_2$)$_2$ | H | 99-100 | 82 | 7.5 | 107.3 ± 3.5; 22.2 ± 1.3 |
| SI-88 | MeS | o-Cl-C$_6$H$_4$CH$_2$ | H | 158-159 | 80 | 3.1 | 101.7 ± 0.9; 102.1 ± 1.2 |
| SI-87 | MeS | p-Cl-C$_6$H$_4$CH$_2$ | H | 126-127 | 75 | 24 | 113.4 ± 1.5; 54.9 ± 2.4 |
| SI-86 | MeS | o-F-C$_6$H$_4$CH$_2$ | H | 133-134 | 72 | 21 | 104.1 ± 1.3; 99.7 ± 0.4 |
| SI-85 | MeS | m-F-C$_6$H$_4$CH$_2$ | H | 113-114 | 71 | 5.2 | 106.2 ± 3.0; 71.3 ± 2.1 |
| SI-84 | MeS | p-F-C$_6$H$_4$CH$_2$ | H | 136-137 | 68 | 4.6 | 102.1 ± 1.4; 99.2 ± 1.0 |
| SI-70 | MeS | C$_6$C$_5$CH$_2$ | Cl | 130-131 | 74 | 3.0 | 52.2 ± 2.4; 24.4 ±2.5 |
| SI-65 | MeS | C$_6$C$_5$CH$_2$ | F | 152-153 | 74 | 35 | 62.7 ± 0.7; 44.4 ± 2.5 |
| SI-83 | MeS | m-Cl-C$_6$H$_4$ | H | 102-103 | 55 | 0.6 | 17.1 ± 1.3; 15.1 ± 0.7 |
| SI-90 | MeS | m-F-C$_6$H$_4$ | H | 212-213 | 43 | 1.4 | 94.8 ± 2.7; 84.3 ± 1.5 |
| SI-91 | MeS | m-Br-C$_6$H$_4$ | H | 250 (dec) | 40 | 1.8 | 100.1 ± 1.1; 84.7 ± 0.3 |
| SI-118 | MeS | C$_6$C$_5$ | H | 169-170 | 60 | 1.2 | 100.1 ± 1.2; 94.4 ± 0.7 |
| SI-96 | EtS | m-Cl-C$_6$H$_4$ | H | 216-217 | 55 | 0.5 | 76.5 ± 1.9; 44.3 ± 1.8 |
| SI-101 | PrS | m-Cl-C$_6$H$_4$ | H | 214-215 | 52 | 1.2 | 77.8 ± 3.0; 6.4 ± 1.9 |
| S-17 | H | m-Cl-C$_6$H$_4$ | H | 202-203 | 62 | 3.8 | 104.1 ±0.4; 101.3 ± 1.5 |
| SI-128 | MeS | m-Br-C$_6$H$_4$ | F | 224-225 | 45 | 4.1 | 63.1 ± 1.1; 55.4 ± 2.0 |
| SI-110 | X$^e$ | CH$_2$C$_6$H$_5$ | H | | | 2.9 | ND |
| SI-136 | Y$^f$ | CH$_2$C$_6$H$_5$ | H | | | 1.2 | ND |
| SI-138 | Y$^f$ | m-F-C$_6$H$_4$CH$_2$ | H | | | 1.5 | ND |
| SI-153 | Z$^g$ | m-Cl-C$_6$H$_4$ | H | | | 0.7 | ND |
| PP2 | | | | | | 0.5 | 36.8 ± 1.7; 36.4 ± 1.6 |

$^a$ $K_i$ (expressed as a µM concentration) toward recombinant human Src were calculated according to the following equation: $K_i = (ID_{50}-E_0/2)/\{E_0-[S_0/K_m-1]/E_0\}$, where $S_0$ is the concentration of the competing substrate (ATP), and $E_0$ is the concentration of the enzyme. Each experiment was in triplicate and mean values were used for the interpolation. Curve fitting was performed with the program GraphPad Prism.
$^b$ Antiproliferative activity of test compounds toward SaOS-2 cells (MTT assay) after 24 and 48 h treatment, expressed as cellular viability (CV, percent value) with respect to control (100%). Values are means ± SD of three independent experiments performed in duplicates.
$^c$ Compounds reported elsewhere.
[18] $^d$ While SI-83 and SI-96 have similar $K_i$ values for Src inhibition, they show a markedly different activity in the cell proliferation assay. Since the replacement of the MeS group with an EtS moiety is expected to have not a great effect on both the solubility and metabolic stability, a reason of the discrepancy in $K_i$ values and cell proliferation activity may be that SI-96 is not able to inhibit Akt, differently from what SI-83 does. In this context, the biological behavior of SI-96 deserves of further investigations.
$^e$ X = SCH$_2$CH$_2$-(4-morpholino).
$^f$ Y = S-cyclopentyl.
$^g$ Z = S-cyclohexyl.

The compounds were tested by MTT assay at a concentration of 25 µM and their effects were evaluated after 48 h (FIG. 1A). PP2 was tested as well on SaOS-2 and proved to cause an inhibition of cell viability of 63.5% respecting to vehicle (DMSO). By BrdU incorporation assay, antiproliferative activities toward SaOS-2 was proved (FIG. 1B). Then, by MTT assay, both SI-83 and PP2 showed a dose-dependent inhibitory capacity of cell viability (FIG. 2, left panels), although apparently with a different potency. The kinetics of induced inhibition seemed to be different for the compounds (FIG. 2, right panels). In particular, at a concentration of 25 µM SI-83 was able to inhibit cell viability of 83%, a percentage of inhibition obtained by PP2 at concentrations higher than 50 µM. The different curve profiles of the activity of the two compounds may be due to different affinities of these molecules for their target Src. IC$_{50}$ values calculated for the two compounds resulted as 8.07 µM for PP2 and 12.64 µM for SI-83. The inhibition curves comprehensive of values obtained with concentrations up to 100 μM confirmed a different mechanism of action of SI-83 respecting to PP2. In fact, PP2 had an initial very steep slope of the curve and then tend to a plateau. On the contrary, SI-83 had a less steep initial trend, showing for low dosages up to 5 μM an activity very lower respecting to PP2, but it then rapidly increased reaching its maximum of activity already at a concentration of 50 μM. These data seem to indicate that SI-83 is a better compound than PP2 in inhibiting cell viability and that the $IC_{50}$ value may not be sufficient to express a qualitative ranking of bioactive compounds If dose-dependence and the maximal value of their activity are not taken into account.

Pyrazolo[3,4-d]Pyrimidines Induce Apoptosis in SaOS-2

Specific pro-apoptotic actions have been reported for Src inhibitors.[23] A TUNEL assay was performed after a 48 h-treatment with different concentrations of PP2 and SI-83. For all the two compounds assayed, a pro-apoptotic effect was evident. The data indicated that, as observed for other cell types,[22,24] PP2 induced apoptosis also in SaOS-2 cells (FIG. 3), probably as a consequence of Src signalling inhibition. The strongest pro-apoptotic effect seemed that of SI-83, also in consideration of the different $IC_{50}$ of the compounds (FIG. 3A-B).

The authors performed flow cytometric assays on SaOS-2 cells, after a treatment with PP2 and SI-83 at different concentrations. As reported, Src is involved in cell cycle progression and in proceeding from G0/G1 to subsequent phases.[25] The compounds tested induced apoptosis, as represented by the presence of G0 cell sub-population (FIG. 3C). PP2 was able to stop cell cycle progression in G0 and G1 phases in a dose-dependent manner, as observed in other cell types.[18, 22-24, 26-33]

Since cytotoxicity may occur as an undesirable side effect of compounds with a potential therapeutic application and contribute to a diminished cell proliferation, the authors evaluated cell morphology changes by the Hoechst assay. As shown in FIG. 3D, PP2 and SI-83 treated cells revealed morphology similar to control even if condensed apoptotic nuclei are visible as well. Taken together these results suggest that Src inhibitors are able to arrest cell growth and induce apoptosis.

The authors' results indicate a role of Src in modulating cell viability, proliferation, cell cycle progression and apoptosis in human osteosarcoma cells. This is in line with what reported by others.[34] In their case the involvement of additional phosphorylations beyond Src is suggested also by the inhibition of the total protein phosphorylation levels induced by pyrazolo[3,4-d]pyrimidine derivatives (data not shown). Their findings are in agreement with what recently reported by Diaz-Montero[35] on the Src activation of the FAK-independent P13K/Akt mediated anoikis resistance of human osteosarcoma cells.

SI-83 pyrazolo[3,4-d]pyrimidine inhibits Src-Y416 phosphorylation in SaOS-2

To verify if SI-83 decreased the Src phosphorylation in drug-treated cells, the authors performed Western Blotting with anti-non-phospho- and anti-phospho-SrcY416 antibodies. The treatment with both PP2 and SI-83 strongly inhibited the phosphorylation of Src at Y416, of 50% and 55%, respectively (FIGS. 4A and 4B). Molecular modeling simulations allowed us to shed light on the possible binding mode of SI-83 into the Src kinase structure. The best docked conformation of this molecule into the ATP binding pocket showed hydrophobic contacts between the m-chlorophenylamino side chain at C4 and the hydrophobic region II of Src, as well as interactions of its methylthio substituent at C6 and Ala390 (FIG. 4C). Finally, part of the N1 side chain was located within the adenine pocket, while its terminal portion pointed toward the hydrophobic region I. Such theoretical results suggested that hydrophobic contacts with both the hydrophobic region I and II could play a pivotal role in determining the affinity for Src.

These results suggest that cell proliferation and induction of apoptosis are modulated by Src activity in SaOS-2 and that anti-proliferative and pro-apoptotic activities of SI-83 work with a molecular mechanism analogous to that of PP2, although potentiated in SI-83, probably due to its molecular structure.

Src is not overexpressed in osteosarcoma and Src overexpression by itself is not sufficient for oncogenic transformation.[35] More generally, even when present, like in colon cancers, Src mutations do not seem the predominant mechanism of Src activation in tumours.[36-38] On the other hand, some findings suggest that enhanced activity of Src family kinases and hyperphosphorylation of paxillin synergistically contribute to the high metastatic potential of osteosarcoma,[7] although a paxillin-independent scenario has also been suggested.[35] A Src role in osteosarcoma has been linked in U2-OS and SaOS-2 cell lines to the antioncogenic role of CD99 through the regulation of caveolin-1 and inhibition of Src activity.[11] Very recently, it has been reported that Src activation/phosphorylation levels do not correlate with osteosarcoma cell lines response to dasatinib, suggesting that low levels of Src kinase activation are sufficient to induce biological properties.[39]

In Primary Human Osteoblasts SI-83 Pyrazolo[3,4-d]Pyrimidine Less Affects Proliferation and Apoptosis Expression of Src and related kinases are important in many physiological processes, thus inhibition of Src could also result in considerable adverse effects in normal cells. For this reason, the authors tested SI-83, the most active compound on SaOS-2 cells, also for its inhibitory activity on cell viability of primary human osteoblastic cells by MTT assay. For osteoblasts treatment both SI-83 and PP2 were used for 48 h at the same concentrations adopted for SaOS-2 cells. The inhibitory activity of PP2 on osteoblasts was quite similar to what observed on SaOS-2 cells (FIGS. 5A and 1A). Differently, SI-83 showed an opposite effect. In fact, when this compound was used at 25 μM the percentage of cell viability was about 80% (65% higher respect of what observed on SaOS-2), while when it was used at 12.5 μM (close to its $IC_{50}$) osteoblast viability was not affected at all. This data suggest that SI-83 may be selective for transformed cells.

To better evaluate the pro-apoptotic activity on osteoblasts the authors also performed a time-course cytofluorimetric analysis, using PP2 and SI-83 at their respective $IC_{50}$, as previously determined on SaOS-2 cells (FIG. 5B). Although an induction of apoptosis was observed, nevertheless SI-83 induced half of apoptosis in osteoblasts respecting to PP2. More importantly, when the respective same concentrations ($IC_{50}$) and times of treatment (48 h) were compared between SaOS-2 and osteoblasts (FIGS. 3C and 5B), the authors could observe a decreased pro-apoptotic effect on osteoblasts respecting to SaOS-2. Moreover, while only a 15% reduction was observed for PP2, a reduction of 79% was observable for SI-83. Finally, it is noteworthy that induced apoptosis was very similar at 48 and 96 h. Hoechst staining confirmed that treatment with SI-83, differently from PP2, did not alter cell morphology or cause DNA damage (FIG. 5C). These remarkable results strongly suggest a different action of SI-83 on primary osteoblasts respecting to osteosarcoma cells. The authors' findings on primary human osteoblasts are in agreement with previous reports proving that osteoblasts derived from Src-knockout mice showed unremarkable bone morphology respecting to wild-type animals[40] or indicating a continuing increasing bone mass skeletal phenotype in Src−/−mice.[41] Proteomic markers of osteoblast differentiation[42] were also found unaltered in SI-83-treated and untreated primary osteoblasts (data not shown). The therapeutic application of Src inhibitors may be of great relevance in bone diseases since the compensation for the loss of Src activity by other members of the Src kinase family in other cell types probably do not occur in bone cells.[43] Therefore, inhibition of Src would be predicted to affect bone without altering the metabolism of other organs.[44]

In Primary Human Osteoblasts SI-83 Pyrazolo[3,4-d]Pyrimidine does not Impair Differentiation and Mineralization Bone matrix is produced and deposed by osteoblasts in bone tissue and the formation of mineralization nodules is one of the most important markers of their differentiation. To evaluate the effect of pyrazolo-pyrimidine derivatives on osteoblast biological functionality, following cell treatment, the deposed $Ca^{2+}$ of the mineralized nodules was quantified, administering PP2 and SI-83 to cells twice a week, in correspondence of medium changes. The authors used concentrations corresponding respectively to $IC_5$, $IC_{20}$ and $IC_{50}$, previously calculated on SaOS-2. The treatments were carried out for three weeks and deposition of $Ca^{2+}$ was measured each week (FIG. 5D).

Cells treated with PP2 did not tolerate drug treatment and started to die and to detach. Moreover, the percentage of $Ca^{2+}$ present inside calcification nodules was always lower than control. This is probably due to toxicity of PP2 on osteoblasts. The treatment with SI-83 was better tolerated since only at the highest concentration used and at the longest time the authors could notice a worse cellular morphology (data not shown).

The increased levels of calcium deposition and nodules formation the authors observed were in line with what reported that targeted disruption of Src-gene in a mouse model enhanced osteoblast differentiation and bone formation.[1] This implies that Src plays an important role in osteoblast proliferation and differentiation whereas it does not appear to modulate cell survival in these cells, being downregulation of Src activity a well-established feature of differentiated osteoblasts.[1, 45-46] The authors' results obtained in human osteoblasts following treatment with SI-83 confirmed such previous results on a murine model and indicate their novel compound as an interesting chemotherapeutic agent for bone sarcomas, able to inhibit osteosarcoma cell proliferation and also stimulating bone formation by normal osteoblasts in a pathological condition where only an inconsistent osteoid matrix is produced instead of a proper functional bone. Based on the authors' and the above reported knowledge, and also as suggested by previous authors,[47] Src could thus be the target of pharmacological treatments of diseased bone cells with good chance of tolerable effects on other organs. Unaltered activity of primary osteoblasts was also confirmed by the analysis of proteome markers of osteoblast differentiation[42] that were similarly expressed in SI-83 treated and untreated cultures (data not shown).

SI-83 Pyrazolo[3,4-d]Pyrimidine Inhibits Cell Viability on Five Human Osteosarcoma Cell Lines Besides its action on SaOS-2 cells, SI-83 also proved to inhibit cell viability of four more human osteosarcoma cell lines (FIG. 6A). In particular, MNNG cells seemed to be even more responsive than SaOS-2 to the activity of the compound. On the other hand, TE-85, U-20S and MG63 were less susceptible to SI-83. The different response of these cell lines may be in agreement with their different phenotype. MNNG and TE-85 are originally derived from the same osteosarcoma patient,[48] but MNNG cell line is a further transformed subclone from TE-85 and has far more malignant features in terms of metastatic and tumorigenic potential than its original clone.[49] MG-63 cells, derived from low-grade osteosarcoma, poorly express TEM7 an important gene associated with metastasis, that is, on the contrary, highly expressed in SaOS-2 and TE-85 cell lines[50] and is the only osteosarcoma cell line not affected by the action of pro-apoptotic dasatinib Src inhibitor.[39] SaOS-2 cells have been reported to be greatly more tumorigenic and metastatic respecting to U-20S.[51] Moreover, SaOS-2 cells may mimic undifferentiated osteoblasts while MG-63 cells may represent a more differentiated stage.[51] This has been also proved by proteomics, indicating that SaOS-2 express proteins typical of immature osteoblasts.[42] Moreover, in human osteosarcoma lines the E promoter of ERalpha transcription is active, except in MG-63, while primary osteoblasts express low levels of ERalpha proteins.[52] These findings are in agreement with the authors' observation that when pyrazolo[3,4-d]pyrimidine derivatives are used on human mature osteoblasts they less affect proliferation and apoptosis.

SI-83 Pyrazolo[3,4-d]Pyrimidine Decreases Osteosarcoma Tumour Mass in a Xenograft Mouse Model In order to evaluate the effect of SI-83 in a preclinical experimental model of osteosarcoma the authors injected s.c. SaOS-2 cells together with Matrigel in nude mice. The SaOS-2 xenograft showed an appreciable growth in the 100% of inoculated mice with a volume doubling time of about 15 days. The daily administration of SI-83 did not determine any appreciable sign of distress or loss of weight in mice (data not shown). The authors divided mice in three groups containing each 4 mice: mice receiving vehicle (control); mice receiving 50 mg/kg SI-83; mice receiving 100 mg/kg SI-83. The administration of SI-83 determined at endpoint a reduction in xenograft growth respect to control measured as weight reduction (FIG. 6B1). At the dose of 100 mg/kg, SI-83 determined a significant reduction ($P<0.01$) in tumour weight of about 40% respect to control tumours. Also the administration of 50 mg/kg SI-83 determined a smaller (about 15%) but significant reduction ($p<0.05$) in tumour volume respect to control (FIG. 6B1). Representative tumours for each group are shown in FIG. 6B2. Xenograft tissues were processed for histologic evaluation of phospho-Src expression (FIG. 6B3). Tumour cells in the control group expressed detectable levels of phospho-Src. On the contrary when we analyzed the tumour tissues from the treated groups the authors detected only a faint or null staining for the phospho-Src antigen (FIG. 6B3).

Inhibition of Normal Osteoblasts

Cells were treated with the test compound (25 µM) for 48 h, following a MTT assay. Osteoblast growth was moderatedly reduced by SI-83 (20%), differently from PP2 that showed a 50% inhibitory activity. It is very important to note that, at the same concentration, the new pyrazolo-pyrimidine showed an antiproliferative activity toward SaOS-2 cells of about 85%, suggesting that it is highly selective in interfering with the proliferation of abnormal osteoblasts. A time-course experiment was also performed to evaluate the pro-apoptotic activity of SI-83, further supporting the hypothesis that the test compound is able to specifically inhibit cell proliferation and to induce apoptosis in transformed cells with respect to normal osteoblasts.

Inhibition of Osteoclasts

Considering that Src-defective osteoclasts showed abnormal organization of cytoskeletal elements necessary for bone resorption, SI-83 was also tested for its ability to influence osteoclast-resorptive activity, in comparison to PP2 (FIG. 7). Compound SI-83 was able to abrogate bone resorption in mouse osteoclasts at 10 and 1 μM concentrations, while percent inhibition was lower but significant also for reduced test dose (up to 1 nM).

It is very important to note that there is a significant difference in bone resorption for the control (DMSO) in the two experiments reported in FIG. 4. In fact, when compound SI-83 was tested, bone resorption in the control group was about 20%, while only a 3% resorption was found in the control group when PP2 was assayed. The method used to measure bone resorption is based on the growth in vitro of osteoclasts that then resorb bone. However, this cell-based assay is usually characterized by a significant variability, mainly due to the fact that the basic amount of bone resorption can vary among replicates. Although such a limitation, this assay is widely recognized as the gold standard to assess the ability of compounds to inhibit bone resorption by osteoclasts.[53]

Mechanistic Studies on Spontaneously-Transformed Tumor Cells from Mice Double Transgenic for c-Myc and c-Raf To enable mechanistic studies, the authors isolated spontaneously-transformed tumor cells from mice double transgenic for c-Myc and c-Raf. Cells were isolated from lung tumors of eight-month-old transgenic mice using the authors' protocol for the isolation and primary culture of rodent respiratory epithelial cells.[21] By day 4, the mRNA for the pulmonary surfactant-associated protein C (Sp-C), which is specifically activated in alveolar epithelium, was detected in non-transgenic cells. After 4-7 days of culture, cells from the transgenic mice exhibited the typical cuboidal phenotype. By day 10, some cells began to attain different morphological characteristics indicating individual phenotypes of tumor cells. From single cuboidal cells, 10 cell lines could be established. Double transgenicity for c-Raf and c-Myc in the cell lines were confirmed by PCR detection of the transgenes. These cell lines express transcripts of Vim and Enol, which are accepted markers of epithelial tumors.

Having these tumor-derived cell lines available, the authors investigated the cytotoxicicty of the following compounds (S-19, SI-88, SI-91, SI-96, SI-110, SI-136, SI-138, SI-153). Since genetic alterations normally occur in cancer cells, the authors first determined by sequencing the presence of any hotspots mutations in Kras and Trp53, two genes implicated in lung cancer, particularly in smokers.[54] The authors did not detect sequence alterations therefore provides further evidence for the stem/native cells of the cell clons.

Cells and Cell Cultures

The human osteosarcoma cell lines SaOS-2, MNNG, U2-OS, TE-85 and MG-63 were obtained from ATCC (HTB-85) and cultured in Dulbecco's Modified Eagle's Medium (DMEM) supplemented with 10% (v/v) fetal calf serum (FCS), at 37° C., 2 mM L-glutamine, penicillin (100 U/ml) and streptomycin (100 μg/ml) (all Sigma-Aldrich, St. Louis, USA), at 37° C., in a humidified atmosphere of 7% CO2/93% air.

Bone samples were obtained from five male patients (average age 55 years old) who underwent total hip replacement surgery. The patients were selected excluding those who have received a previous therapy with hormone replacement or glucocorticoid treatment during the previous 2 years. Trabecular bone fragments were extensively washed in phosphate buffered saline (PBS; Sigma-Aldrich) to remove blood and bone marrow and then explanted into culture containing DMEM supplemented with 10% (v/v) FCS, 2 mM L-glutamine (Gibco), penicillin (100 U/ml) and streptomycin (100 μg/ml). Cultures were carried out as reported.[42, 53] The cells obtained with this method were positive for alkaline phosphatase activity and expression of osteoblast differentiation markers.[42, 55]

Cell Treatments

Pyrazolo[3,4-d]pyrimidine derivatives were dissolved in dimethyl sulphoxide (DMSO) (Sigma-Aldrich) at various concentrations and diluted in cell culture medium prior to use. PP2 (Calbiochem, Darmstadt, Germany) was parallely used as a reference compound. Controls were carried out with DMSO concentrations corresponding to the higher doses of the test compounds. The final DMSO concentration did not exceed 0.2% (v/v) and did not affect the parameters analysed. Cells were treated when at confluence.

Cell Viability Assays

Cell viability was quantified by the MTT ([3-(4,5-dimethylthiazol-2-yl)-2,5-diphenyltetrazolium bromide]) assay (Molecular Probes-Invitrogen Corporation, Carlsbad, USA). Cells (about $3 \times 10^4$ for each well) were seeded in 96 multiwell plate with culture medium and then exposed to compounds at concentration 25 μM for 48 h. The medium was removed and the cells were incubated for 4 h with fresh medium in the presence of 1.2 mM MTT. After solubilization in DMSO, the absorbance of the formazan was measured with a microplate absorbance reader at 540 nm. The inhibitory activity of the compounds was compared with that of PP2, used at the same concentrations of compounds. To evaluate $IC_{50}$ for SI-83 and PP2 cells were assayed by MTT and the percentage of inhibition of cell viability at various concentrations (1 μM-100 μM) for 48 h was evaluated.

Cell viability was quantified by MTT on human osteoblasts. About 30.000 cell were seeded in a 24 multiwell plate, grown for 7 days (confluence) and then exposed for 48 h to compounds at concentration equal to $IC_{50}$, calculated on SaOS-2 cells as reported above. DNA duplication was assessed using a colorimetric immunoassay kit to quantify the incorporation of 5-bromo-2'-deoxyuridine (BrdU) during DNA synthesis (Roche Applied Science, Mannheim, Germany). This assay was performed on cells previously treated for 24 h with SI-83 at both 12.5 and 25 μM concentrations. Briefly, BrdU was added to the cells for 18 h before the end of the treatment. Fixation and partial DNA denaturation was performed before staining with anti-BrdU antibody. Immune complexes were detected by subsequent substrate reaction and the absorbance was measured using a multiwell spectrophotometer (BioRad).

Apoptosis and Cell Cycle Assays

The DNA strand breaks in the apoptotic cells were assayed by the TUNEL in situ cell death detection kit (Roche Applied Science, Mannheim, Germany). SaOS-2 cells were grown on coverslips placed in sterile shell vials (Sarstedt, Nümbrecht, Germany) and treated with PP2 and SI-83, as well as with DMSO as negative control, at concentration 12.5 μM for 48 h. The TUNEL assay was then performed according to the manufacturer's instruction. Pictures were taken and apoptotic nuclei counted. For each sample 5 independent pictures were taken.

The percentage of apoptotic cells was evaluated by FACS analysis. $1 \times 10^6$ SaOS-2 cells were plated in 6-well multiplates and grown in complete medium until confluence. Two different treatments where done for SaOS-2 and for primary osteoblasts. SaOS-2 were treated for 48 h with compounds at concentrations of 3 μM, 25 μM, 100 μM and $IC_{50}$. Primary osteoblasts were treated at concentration equal to $IC_{50}$ calculated on SaOS-2 cells as described for 24, 48 and 96 h. After treatment cells were washed 3 times in PBS and fixed o.n. in ice-cold 70% (v/v) ethanol at −20° C. The cell suspension was centrifuged, washed twice with 1 mL of PBS and resuspended in 1 mL of PBS containing ribonuclease (Type-1A, 1 mg/mL; Sigma-Aldrich) and propidium iodide (PI, 50 µg/mL; Sigma-Aldrich). The tubes were placed on ice in the dark until the cellular orange fluorescence of PI was collected in a linear scale using a FACS-calibur flow cytometer (Becton Dickinson, Franklin Lakes, USA) equipped with an excitation laser line at 488 nm and a 575±15 nm band pass filter. At least 20.000 events were collected for each sample using the Cell Quest software (Becton Dickinson) and the pulse processing module for doublet discrimination; debris was excluded from the analysis by an appropriate morphological gate of forward scatter vs side scatter.

Hoechst staining was used to evaluate healthy, necrotic and apoptotic cell morphology. About $2 \times 10^5$ cells were seeded on 8 chamber polystyrene vessels (BD Falcon, Bedford, USA), grown in complete medium until confluence, and then exposed to PP2, SI-83 and S-7 at concentration 25 µM for 48 h. Then cells were fixed 15 min in 4% paraformaldehyde, washed in PBS, air dried and incubated for 10 min with 10 µg/ml Hoechst 33342 (Invitrogen, Paisley, UK), a bisbenzimide cell-permeant dye that fluoresces bright blue upon binding to DNA. The coverslips were rinsed five times in distilled water and let air dry in the dark. Coverslips were then mounted using PBS/glycerol and examined by fluorescence microscopy and digital image capture.

Immunoblotting

For Phospho-SrcY416 detection, cells were lysed in ice-cold 0.1% SDS containing a cocktail of protease inhibitors and 1 mM sodium orthovanadate (Sigma-Aldrich). 10-20 µg of cell cultures protein lysates, diluted in reducing buffer, were resolved by 12% SDS-PAGE and electrotransferred onto nitrocellulose. All antibodies employed were from Cell Signaling Technology (Denver, USA). Proteins were probed with primary antibodies o.n. at 4° C., followed by secondary antibodies for 1 h at room temperature. Detection was obtained by ImmunoStar HRP™ (BioRad). Band areas were detected using ImageScanner™ (Amersham Bioscience, Little Chalfont, GB) and bands' optical densities were analysed by ImageMaster software (Amersham Bioscience). Band optical densities of Phospho-SrcY416 were normalized against those of total Src as an internal control.

Nodules Formation and Mineralization

The mineralized nodule formation and their degree of mineralization were determined for osteoblasts grown in 6-well plates for 7, 14, 21 days using alizarin red S staining Cells were treated with PP2 and SI-83 at their respective $IC_{50}$, $IC_{20}$ and $IC_5$, calculated on SaOS-2 cell. The compounds administration was repeated every 3 days, in correspondence with medium changes. Briefly, after two washes with PBS, cells were fixed with ice-cold 70% (v/v) ethanol for 1 h, washed again and stained with 40 mM alizarin red S (Sigma-Aldrich) in deionized water (adjusted to pH 4.2) for 10 min. Cells were rinsed with PBS and destained for 15 min with 10% (w/v) cetylpyridinium chloride in 10 mM sodium phosphate (pH 7.0). The extracted stain was transferred to a 96-well plate and the absorbance at 562 nm was measured using a plate/reader spectrophotometer.

SaOS-2 Xenograft

CD 1 nude mice (Charles River, Milan, Italy) were maintained under the guidelines established by the authors' Institution (University of L'Aquila, Medical School and Science and Technology School Board Regulations, complying with the Italian government regulation n.116 Jan. 27, 1992 for the use of laboratory animals). Before tumour cells implantation, mice were anesthesized with a mixture of ketamine (25 mg/mL)/xylazine (5 mg/mL). Xenografts were obtained by injecting s.c. $1 \times 10^6$ SaOS-2 cells in 100 µL of 12 mg/ml Matrigel (Becton Dickinson). Mice received daily the drug by per os administration at the doses indicated. Tumour growth was monitored daily and at the endpoint, after 26 days, the tumors were excided, weighted and processed for histology. Briefly tumors were fixed in 4% formaldehyde in 0.1 M phosphate buffer, pH 7.2 and embedded in paraffin. Slide-mounted tissue sections (4 µm thick) were deparaffinized in xylene and hydrated serially in 100, 95, and 80% ethanol. Endogenous peroxidases were quenched in 3% $H_2O_2$ in PBS for 1 h and then slides were incubated with anti human Src [pY416] phosphospecific antibody (Biosource, Camarillo, Calif., USA) for 1 h at room temperature. Sections were washed three times in PBS and antibody binding was revealed using the Sigma fast 3,3'-diaminobenzidine tablet set (Sigma).

Mechanistic Studies on Spontaneously-Transformed Tumor Cells from Mice Double Transgenic for c-Myc and c-Raf Chemicals SI-compounds were dissolved in dimethyl sulfoxide (DMSO) and stored at −20° C. until usage.

The eleven lung tumor cells lines of transgenic mice (double c-myc and c-raf) were cultured in Dulbecco's Modified Eagle's Medium (DMEM), containing 10% fetal calf serum, 100 units/mL streptomycin, 100 units/mL penicillin, 2 mM L-glutamine. Cells were grown in a humidified atmosphere containing 5% $CO_2$ at 37° C.

Cytotoxicity Assay

The cytotoxic activity of eight different compounds was determined by usage of MTS-assay. Cells were plated in 96-well microplates at a density of $2-4 \times 10^3$ cells/well. Afterwards, the cells were allowed to attach for 24 h. The experimental drugs were freshly prepared in DMEM at five different concentrations (0 µM, 0.1 µM, 1 µM, 10 µM, 100 µM) and were added to 96-well-plates in quadruplicates at a volume of 100 µL each well. Following, the cells were incubated for 24 h at 37° C. and 5% $CO_2$. For cytotoxicity assay, 20 µL of the CellTiter 96® AQueous One Solution Reagent (Promega Corporation, Madison, Wis., USA) were added per well and the plates were incubated for 1 h at 37° C. The CellTiter 96® AQueous One Solution Reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). PES has enhanced chemical stability, which allows it to combine with MTS to form a stable solution. In metabolically active cells, the MTS tetrazolium compound is bioreduced by dehydrogenase enzymes into a coloured formazan product.

The absorbance of the formazan product was detected at 490 nm on the plate spectrometer (Victor$^3$ 1420 Multible Counter, Perkin Elmer Instruments, Shelton, USA) and is commensurate to the number of living cells. The cytotoxicity assays were also performed for a total time span of 96 h. Therefore, cells were plated in 96-well plates at a density of 100-500 cells/well at the beginning of the incubation. Cells were allowed to attach and were incubated with the drugs every 24 h.

Cell Cycle Analysis

The effect of the eight different compounds on the cell cycle was studied using flow cytometry analysis. Cells were plated in 6-well plastic plates at a density of $1.25-2.50 \times 10^5$ cells/well. Cells were allowed to attach for 24 h. Following, cells were treated with drugs for 24 h at 37° C. and 5% $CO_2$. Cells were harvested by trypsinisation and DNA-preparation was performed with the CycleTEST PLUS DNA Reagent Kit (Becton Dickinson Immunocytometry Systems, San Jose, Calif.). Likewise to the manufacturers' procedure-protocol, the cells were washed with buffer solution containing DMSO, sodium citrate and sucrose. Then, cells were incubated consecutively with:

Solution A for 10 min at rt (contains trypsin in a spermine tetrahydrochloride detergent buffer to digest cell membranes and cytoskeletons), Solution B for 10 min at rt (contains trypsin inhibitor and ribonuclease A in citrate-stabilizing buffer with spermine tetrahydrochloride to inhibit the trypsin activity and to digest the RNA), Solution C for 15 min at 4° C. (contains propidium iodide and spermine tetrahydrochloride in citrate stabilizing buffer).

DNA content was analyzed on a flow cytometer by fluorescence-activated cell sorting analysis (FACSan, Becton Dickinson GmbH Immunzytometrische Systeme, Heidelberg, Germany) using ModFit software (Verity Software House, Inc.).

References
1. Marzia, M. et al., *J. Cell. Biol.* 2000, 151, 311-320.
2. Almeida, M. et al., *J. Biol. Chem.* 2005, 280, 41342-41351.
3. Vertino, et al., *J. Biol. Chem.* 2005, 280, 14130-14137.
4. Soriano, P et al., *Cell* 1991, 64, 693-702.
5. Boyce, B. F. et al., *J. Clin. Invest.* 1992, 90, 1622-1627.
6. Klein, B. Y. et al., *J. Cell. Biochem.* 2006, 98, 661-671.
7. Azuma, K. et al., *Oncogene* 2005, 24, 4754-4764.
8. Missbach, M. et al., *Bone* 1999, 24, 437-449.
9. Grey, A. et al., *Expert Opin. Investig. Drugs* 2005, 14, 265-278.
10. Jin, U. H. et al., *J. Ethnopharmacol.* 2006, 106, 333-343.
11. Manara, M. C. et al., *Mol. Biol. Cell* 2006, 17, 1910-1921.
12. Metcalf, C. A, et al., *Curr. Pharm. Des.* 2002, 8, 2049-2075.
13. Barrios Sosa, A. C. et al., *Bioorg. Med. Chem. Lett.* 2005, 15, 1743-1747.
14. Plé, P. A. et al., *J. Med. Chem.* 2004, 47, 871-887.
15. Altmann, E. et al., *Mini Rev. Med. Chem.* 2002, 2, 201-208.
16. Hanke, J. H. et al., *J. Biol. Chem.* 1996, 271, 695-701.
17. Bondavalli, F et al., WO2004106340.
18. a) Carraro, F. et al., *J. Med. Chem.* 2006, 49, 1549-1561. b) Angelucci, A. et al., *Eur. J. Cancer* 2006, 42, 2838-2845.
19. Huntly, B. J.; Gilliland, D. G. *Nature* 2005, 435, 1169-1170.
20. Al-Hajj, M. et al., *Proc. Natl. Acad. Sci. USA* 2003, 100, 3983-3988.
21. Hansen, T. et al., *Toxicol. Vitro* 2006, 20, 757-766.
22. Schenone, S. et al., *Eur. J. Med. Chem.* 2004, 39, 939-964.
23. Carraro, F et al., *J. Med. Chem.* 2004 47, 1595-1598.
24. Schenone, S. et al., *Bioorg. Med. Chem. Lett.* 2004, 14, 2511-2517.
25. Moasser, M. M. et al., *Cancer Res.* 1999, 59, 6145-6152.
26. Golubovskaya, V. M. et al., *Mol. Cancer. Res.* 2003, 1, 755-764.
27. Liu, Z. et al., *J. Clin. Endocrinol. Metab.* 2004, 89, 3503-3509.
28. Boyd, D. D., et al., *Clin. Cancer. Res.* 2004, 10, 1545-1555.
29. Angers-Loustau, A. et al., *Mol. Cancer. Res.* 2004, 2, 595-605.
30. Contri, A. et al., *J. Clin. Invest.* 2005, 115, 369-78.
31. Lee, M. et al., *J. Cell. Biochem.* 2004, 93, 629-638.
32. Nam, J. S. et al., *Clin. Cancer. Res.* 2002, 8, 2430-2436.
33. Schenone, S. et al., *Eur. J. Med. Chem.* 2004, 39, 153-160.
34. Ren, S. et al., *Biochem. Biophys. Res. Commun.* 2003, 308, 120-125.
35. Diaz-Montero, C. M. et al., *Eur. J. Cancer* 2006, 42, 1491-1500.
36. Brunton, V. G. et al., *Cancer Res.* 2005, 65, 1335-1342.
37. Daigo, Y. et al., *Cancer Res.* 1999, 59, 4222-4224.
38. Nilbert, M., and Femebro, E. *Cancer Genet. Cytogenet.* 2000, 121, 94-95.
39. Shor, A. C. et al., *Cancer Res.* 2007, 67, 2800-2808.
40. Lowe, C. et al., *Proc. Natl. Acad. Sci. USA* 1993, 90, 4485-4489.
41. Amling, M. et al., *Bone* 2000, 27, 603-610.
42. Spreafico, A. et al., *Proteomics* 2006, 6, 3520-3532.
43. Perez, M. et al., *Eur. J. Cancer* 2001, 37, 629-640.
44. Šuša, M. et al., *Drug News Perspect.* 2000, 13, 169-175.
45. Zaidi, S. K. et al., *EMBO J.* 2004, 23, 790-799.
46. Longo, M. et al., *Bone* 2004, 34, 100-111.
47. Recchia, I. et al., *Bone* 2004, 34, 65-79.
48. McAllister, R. M et al., *Cancer* 1971, 27, 397-402.
49. Luu, H. H. et al., *Clin. Exp. Metast.* 2005, 22, 319-329.
50. Fuchs, B., et al., *Article in press*.
51. Orimo, H., and Shimada, T. *Mol. Cell. Biol.* 2006, 282, 101-108.
52. Longo, M. et al., *J. Mol. Endocrinol.* 2006, 37, 489-502.
53. Takada, Y. et al., *Bone Miner.* 1992, 17, 347-359.
54. Le Calvez, F. et al., *Cancer Res.* 2005, 65, 5076-5083.
55. Frediani, B. et al., *Bone* 2004, 35, 859-869.
56. La Rosée, P. et al., *Cancer Res.* 2002, 62, 7149-7153.

The invention claimed is:
1. A compound having the formula:

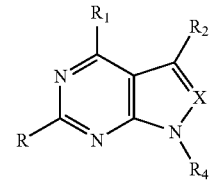

wherein
R represents H, alkylthio, alkylamino, cycloalkylthio, cycloalkylamino, $S(CH_2)_nOH$, $S(CH_2)_nNH_2$, $NH(CH_2)_n OH$, or $NH(CH_2)_nNH_2$;

$R_1$ represents NH—$R_6$ or $N(R_6)_2$;

$R_6$ represents an aryl with the formula:

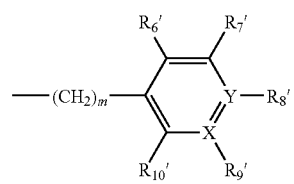

in which X and Y are independently C or N;

$R_6'$, $R_7'$, $R_8'$, $R_9'$, $R_{10}'$ are independently H, —$C_{1-6}$ alkyl, $C_{2-6}$ alkenyl, $C_{2-6}$ alkynyl, aryl substituted groups, halo, haloalkyl, $OCH_3$, $NO_2$, CN, $CONH_2$, CONH—$C_{1-6}$ alkyl, $CON(C_{1-6}$ alkyl$)_2$, $NH_2$, NH—$C_{1-6}$ alkyl, $N(C_{1-6}$ alkyl$)_2$, NHC(O)alkyl, $NHSO_2$—$C_{1-6}$ alkyl, $SO_2NH_2$, $SO_2NHC_{1-6}$ alkyl, $SO_2N(C_{1-6}$ alkyl$)_2$, OZ' or SZ' where Z' is H, or alkyl, aryl or aralkyl substituted group, m is comprised between 0 and 4, provided that when X and Y are C, at least one of $R_6'$, $R_7'$, $R_8'$, $R_9'$, and $R_{10}'$ is $C_{1-6}$ alkyl, $OCH_3$, or halogen;

$R_2$ represents H;
$R_4$ represents

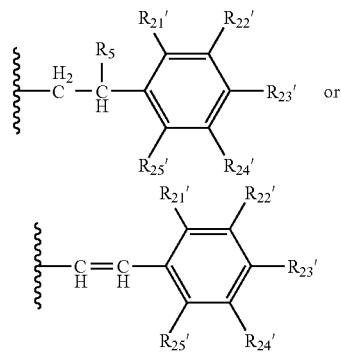

wherein
wherein $R_{21}'$, $R_{22}'$, $R_{23}'$, $R_{24}'$, $R_{25}'$ are independently H, or halo; and
$R_5$ represents Cl, Br, OH, H, $CH_3$.

2. A compound of claim 1 represented by formula presented below selected from the group consisting of:

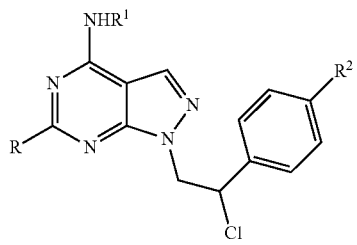

Compound S-29: wherein R=H, $R^1$=p-F—$C_6H_4CH_2$, $R^2$=Cl;
Compound SI-56: wherein R=MeS, $R^1$=m-F—$C_6H_4(CH_2)_2$, $R^2$=H;
Compound SI-59: wherein R=MeS, $R^1$=o-Cl—$C_6H_4(CH_2)_2$, $R^2$=H;
Compound SI-58: wherein R=MeS, $R^1$=m-Cl—$C_6H_4(CH_2)_2$, $R^2$=H;
Compound SI-57: wherein R=MeS, $R^1$=p-Cl—$C_6H_4(CH_2)_2$, $R^2$=H;
Compound SI-60: wherein R=MeS, $R^1$=p-Me-$C_6H_4(CH_2)_2$, $R^2$=H;
Compound SI-61: wherein R=MeS, $R^1$=p-MeO—$C_6H_4(CH_2)_2$, $R^2$=H;
Compound SI-88: wherein R=MeS, $R^1$=o-Cl—$C_6H_4CH_2$, $R^2$=H;
Compound SI-87: wherein R=MeS: $R^1$=p-Cl—$C_6H_4CH_2$, $R^2$=H;
Compound SI-86: wherein R=MeS, $R^1$=o-F—$C_6H_4CH_2$, $R^2$=H;
Compound SI-85: wherein R=MeS, $R^1$=m-F—$C_6H_4CH_2$, $R^2$=H;
Compound SI-84: wherein R=MeS, $R^1$=p-F—$C_6H_4CH_2$, $R^2$=H;
Compound SI-83: wherein R=MeS, $R^1$=m-Cl—$C_6H_4$, $R^2$=H;
Compound SI-90: wherein R=MeS, $R^1$=m-F—$C_6H_4$, $R^2$=H;
Compound SI-91: wherein R=MeS, $R^1$=m-Br—$C_6H_4$, $R^2$=H;
Compound SI-96: wherein R=EtS, $R^1$=m-Cl—$C_6H_4$, $R^2$=H;
Compound SI-101: wherein R=PrS, $R^1$=m-Cl—$C_6H_4$, $R^2$=H;
Compound S-17: wherein R=H, $R^1$=m-Cl—$C_6H_4$, $R^2$=H;
Compound SI-128: wherein R=MeS, $R^1$=m-Br—$C_6H_4$, $R^2$=F; Compound SI-138: wherein R=S-cyclopentyl, $R^1$=m-F—$C_6H_4$, $R^2$=H, and
Compound SI-153: wherein R=S-cyclohexyl, $R^1$=m-Cl—$C_6H_4$, $R^2$=H.

3. A pharmaceutical composition comprising a compound according to claim 1 or a pharmaceutically acceptable salt thereof and suitable excipients and/or diluents.

* * * * *

UNITED STATES PATENT AND TRADEMARK OFFICE
CERTIFICATE OF CORRECTION

PATENT NO. : 8,466,164 B2  Page 1 of 1
APPLICATION NO. : 12/678021
DATED : June 18, 2013
INVENTOR(S) : Silvia Schenone et al.

It is certified that error appears in the above-identified patent and that said Letters Patent is hereby corrected as shown below:

In the Claims

Column 26, line 35 in claim 1,

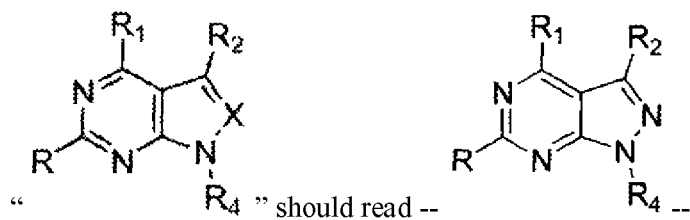

Signed and Sealed this
Twenty-second Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO.       : 8,466,164 B2                                                                 Page 1 of 1
APPLICATION NO.  : 12/678021
DATED            : June 18, 2013
INVENTOR(S)      : Schenone et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 185 days.

Signed and Sealed this
Eighth Day of September, 2015

Michelle K. Lee
*Director of the United States Patent and Trademark Office*